(12) United States Patent
Hercouet

(10) Patent No.: US 7,909,887 B2
(45) Date of Patent: Mar. 22, 2011

(54) METHOD FOR DYEING IN THE PRESENCE OF AT LEAST ONE OXIDIZING AGENT AND AT LEAST ONE ORGANIC AMINE, DEVICE FOR USE THEREOF AND READY-TO-USE COMPOSITION

(75) Inventor: Leïla Hercouet, Neuilly Plaisance (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/339,820

(22) Filed: Dec. 19, 2008

(65) Prior Publication Data

US 2009/0158533 A1 Jun. 25, 2009

Related U.S. Application Data

(60) Provisional application No. 61/006,483, filed on Jan. 16, 2008.

(30) Foreign Application Priority Data

Dec. 21, 2007 (FR) ..................... 07 60277

(51) Int. Cl.
*A61Q 5/10* (2006.01)
(52) U.S. Cl. .............. 8/405; 8/406; 8/435; 8/459; 8/462; 8/463; 8/551; 8/580; 8/597
(58) Field of Classification Search .............. 8/405, 406, 8/435, 459, 462, 463, 551, 580, 597; 132/202, 132/208
See application file for complete search history.

(56) References Cited

U.S. PATENT DOCUMENTS

| | | | |
|---|---|---|---|
| 3,100,739 A | 8/1963 | Kaiser et al. |
| 3,369,970 A | 2/1968 | McLaughlin et al. |
| 3,629,330 A | 12/1971 | Brody et al. |
| 3,861,868 A | 1/1975 | Milbrada |
| 4,138,478 A | 2/1979 | Reese et al. |
| 4,170,637 A | 10/1979 | Pum |
| 4,226,851 A | 10/1980 | Sompayrac |
| 4,357,141 A | 11/1982 | Grollier et al. |
| 4,366,099 A | 12/1982 | Gaetani et al. |
| 4,488,564 A | 12/1984 | Grollier et al. |
| 4,725,282 A | 2/1988 | Hoch et al. |
| 4,845,293 A | 7/1989 | Junino et al. |
| 5,021,066 A | 6/1991 | Aeby et al. |
| 5,259,849 A | 11/1993 | Grollier et al. |
| 5,364,414 A | 11/1994 | Lang et al. |
| 5,817,155 A | 10/1998 | Yasuda et al. |
| 6,010,541 A | 1/2000 | De La Mettrie et al. |
| 6,074,439 A | 6/2000 | De La Mettrie et al. |
| 6,129,770 A | 10/2000 | Deutz et al. |
| 6,156,713 A | 12/2000 | Chopra et al. |
| 6,165,444 A | 12/2000 | Dubief et al. |
| 6,190,421 B1 | 2/2001 | Rondeau et al. |
| 6,206,935 B1 | 3/2001 | Onitsuka et al. |
| 6,238,653 B1 | 5/2001 | Narasimhan et al. |
| 6,251,378 B1 | 6/2001 | Laurent et al. |
| 6,260,556 B1 | 7/2001 | Legrand et al. |
| 6,277,154 B1 | 8/2001 | Lorenz |
| 6,277,155 B1 | 8/2001 | De La Mettrie et al. |
| 6,365,136 B1 | 4/2002 | Lauscher et al. |
| 6,423,100 B1 | 7/2002 | Lang et al. |
| 6,447,552 B1 | 9/2002 | Golinski |
| 6,645,258 B2 | 11/2003 | Vidal et al. |
| 6,660,045 B1 | 12/2003 | Hoeffkes et al. |
| 6,695,887 B2 | 2/2004 | Cottard et al. |
| 6,800,098 B1 | 10/2004 | Allard et al. |
| 7,135,046 B2 | 11/2006 | Audousset |
| 7,153,331 B2 | 12/2006 | Desenne et al. |
| 7,217,298 B2 | 5/2007 | Legrand et al. |
| 7,285,137 B2 | 10/2007 | Vidal et al. |
| 7,442,215 B2 | 10/2008 | Audousset et al. |
| 7,458,993 B2 | 12/2008 | Cottard et al. |
| 7,494,513 B2 | 2/2009 | Kravtchenko et al. |

(Continued)

FOREIGN PATENT DOCUMENTS

CA 1 268 421 5/1990

(Continued)

OTHER PUBLICATIONS

STIC Search Report dated Jan. 21, 2010.*
French Search Report for FR 0760277, dated Aug. 20, 2008.
Copending U.S. Appl. No. 12/339,753, filed Dec. 19, 2008.
Copending U.S. Appl. No. 12/339,781, filed Dec. 19, 2008.
Copending U.S. Appl. No. 12/642,412, filed Dec. 18, 2009.
Copending U.S. Appl. No. 12/642,451, filed Dec. 18, 2009.
Copending U.S. Appl. No. 12/642,468, filed Dec. 18, 2009.
Copending U.S. Appl. No. 12/642,473, filed Dec. 18, 2009.
Copending U.S. Appl. No. 12/642,480, filed Dec. 18, 2009.
Copending U.S. Appl. No. 12/642,489, filed Dec. 18, 2009.
Copending U.S. Appl. No. 12/642,492, filed Dec. 18, 2009.
Copending U.S. Appl. No. 12/642,506, filed Dec. 18, 2009.
Copending U.S. Appl. No. 12/642,513, filed Dec. 18, 2009.
Copending U.S. Appl. No. 12/642,531, filed Dec. 18, 2009.
Copending U.S. Appl. No. 12/642,536, filed Dec. 18, 2009.
Copending U.S. Appl. No. 12/642,543, filed Dec. 18, 2009.
Copending U.S. Appl. No. 12/642,551, filed Dec. 18, 2009.
Copending U.S. Appl. No. 12/642,555, filed Dec. 18, 2009.

(Continued)

*Primary Examiner* — Eisa B Elhilo
(74) *Attorney, Agent, or Firm* — Finnegan, Henderson, Farabow, Garrett & Dunner, LLP

(57) ABSTRACT

A novel process for dyeing human keratin fibers in the presence of an oxidizing agent, comprising applying to the fibers at least one anhydrous composition (A) comprising at least one fatty substance, at least one organic amine having a pKb less than 12 at 25° C., and at least one surfactant, at least one composition (B) comprising at least one oxidizing agent, and at least one composition (C) comprising at least one dye chosen from oxidation dyes and direct dyes; a multi-compartment device or kit, wherein at least one first compartment comprises the at least one anhydrous cosmetic composition (A), at least one second compartment comprises at least one composition (B), and at least one third compartment comprises at least one composition (C); and a ready-to-use composition for dyeing human keratin fibers, comprising at least 35% by weight of at least one fatty substance, at least one organic amine having a pKb less than 12 at 25° C., at least one surfactant, at least one dye chosen from oxidation dyes and direct dyes, and at least one oxidizing agent.

26 Claims, No Drawings

U.S. PATENT DOCUMENTS

| | | | |
|---|---|---|---|
| 7,575,605 B2 | 8/2009 | Legrand | |
| 7,651,533 B2 | 1/2010 | Legrand | |
| 7,651,536 B2 | 1/2010 | Cottard et al. | |
| 7,766,977 B2 | 8/2010 | Cottard et al. | |
| 2003/0190297 A1 | 10/2003 | Narasimhan et al. | |
| 2003/0226217 A1 | 12/2003 | Bowes et al. | |
| 2004/0103488 A1 | 6/2004 | Yamashita et al. | |
| 2004/0105830 A1 | 6/2004 | Boswell et al. | |
| 2004/0181883 A1 | 9/2004 | Legrand et al. | |
| 2004/0226110 A1 | 11/2004 | Legrand | |
| 2005/0129652 A1 | 6/2005 | Keller et al. | |
| 2005/0165705 A1 | 7/2005 | Lauper et al. | |
| 2005/0196367 A1 | 9/2005 | Ohta et al. | |
| 2006/0042023 A1 | 3/2006 | Machida | |
| 2006/0075580 A1 | 4/2006 | Chan et al. | |
| 2006/0137111 A1 | 6/2006 | Au et al. | |
| 2006/0242773 A1 | 11/2006 | Kravtchenko et al. | |
| 2006/0260071 A1 | 11/2006 | Legrand | |
| 2006/0265817 A1* | 11/2006 | Legrand | 8/405 |
| 2007/0006397 A1 | 1/2007 | Schmenger et al. | |
| 2007/0033743 A1 | 2/2007 | Kravtchenko et al. | |
| 2007/0104672 A1 | 5/2007 | Decoster et al. | |
| 2007/0169285 A1 | 7/2007 | Narasimhan et al. | |
| 2007/0275927 A1 | 11/2007 | Philippe | |
| 2007/0277331 A1 | 12/2007 | Goldstein et al. | |
| 2008/0016627 A1 | 1/2008 | Cottard et al. | |
| 2008/0071092 A1 | 3/2008 | Vidal et al. | |
| 2008/0229512 A1 | 9/2008 | Syed | |
| 2008/0256724 A1 | 10/2008 | Bolton et al. | |
| 2009/0007347 A1 | 1/2009 | Cottard et al. | |
| 2009/0060855 A1 | 3/2009 | Boche et al. | |
| 2009/0151086 A1 | 6/2009 | Brun | |
| 2009/0151087 A1 | 6/2009 | Mario et al. | |
| 2009/0158533 A1 | 6/2009 | Hercouet | |
| 2009/0162309 A1 | 6/2009 | Hercouet et al. | |
| 2009/0191142 A1 | 7/2009 | Hercouet et al. | |

FOREIGN PATENT DOCUMENTS

| | | |
|---|---|---|
| CA | 2 573 567 | 3/2006 |
| CH | 507 713 | 7/1971 |
| DE | 20 05 076 | 8/1970 |
| DE | 38 14 356 | 9/1988 |
| DE | 38 14 685 | 9/1988 |
| DE | 43 09 509 | 9/1994 |
| DE | 195 27 121 | 1/1997 |
| DE | 197 23 538 | 9/1998 |
| DE | 197 12 980 | 10/1998 |
| DE | 197 54 281 | 6/1999 |
| DE | 198 15 338 | 9/1999 |
| DE | 100 08 640 | 8/2000 |
| DE | 199 09 661 | 9/2000 |
| DE | 199 62 869 | 6/2001 |
| DE | 100 28 723 | 12/2001 |
| DE | 100 56 266 | 5/2002 |
| DE | 101 48 571 | 4/2003 |
| DE | 101 48 671 | 4/2003 |
| DE | 20 2005 008 307 | 7/2005 |
| DE | 10 2005 011 459 | 9/2006 |
| DE | 10 2005 032 798 | 1/2007 |
| DE | 10 2006 012 575 | 2/2007 |
| DE | 10 2005 059 647 | 6/2007 |
| DE | 10 2006 020 050 | 10/2007 |
| DE | 10 2006 061 830 | 6/2008 |
| EP | 0 166 100 | 1/1986 |
| EP | 0 424 261 | 4/1991 |
| EP | 0 890 355 | 1/1999 |
| EP | 1 023 891 | 8/2000 |
| EP | 1 142 563 | 10/2001 |
| EP | 1 166 749 | 1/2002 |
| EP | 1 219 285 | 7/2002 |
| EP | 1 291 006 A1 | 3/2003 |
| EP | 1 314 418 | 5/2003 |
| EP | 1 321 132 | 6/2003 |
| EP | 1 374 842 | 1/2004 |
| EP | 1 430 873 | 6/2004 |
| EP | 1 438 951 A1 | 7/2004 |
| EP | 1 449 512 | 8/2004 |
| EP | 1 486 195 | 12/2004 |
| EP | 1 488 781 | 12/2004 |
| EP | 1 550 656 | 7/2005 |
| EP | 1 568 354 | 8/2005 |
| EP | 1 570 833 | 9/2005 |
| EP | 1 598 052 A1 | 11/2005 |
| EP | 1 707 184 | 10/2006 |
| EP | 1 716 839 | 11/2006 |
| EP | 1 716 840 | 11/2006 |
| EP | 1 733 759 | 12/2006 |
| EP | 1 762 222 | 3/2007 |
| EP | 1 792 602 | 6/2007 |
| EP | 1 813 254 | 8/2007 |
| EP | 1 862 198 | 12/2007 |
| EP | 1 870 085 | 12/2007 |
| EP | 1 902 703 | 3/2008 |
| EP | 1 927 377 | 6/2008 |
| EP | 1 944 009 | 7/2008 |
| EP | 2 005 939 | 12/2008 |
| EP | 2 011 474 | 1/2009 |
| EP | 2 018 848 | 1/2009 |
| EP | 2 072 034 | 6/2009 |
| EP | 2 072 035 | 6/2009 |
| EP | 2 072 036 | 6/2009 |
| FR | 1 517 715 | 3/1968 |
| FR | 2 132 214 | 11/1972 |
| FR | 2 402 446 | 4/1979 |
| FR | 2 496 458 | 6/1982 |
| FR | 2 616 324 | 12/1988 |
| FR | 2 769 835 | 4/1999 |
| FR | 2 779 949 | 12/1999 |
| FR | 2 803 196 | 7/2001 |
| FR | 2 842 101 | 1/2004 |
| FR | 2 870 724 | 12/2005 |
| FR | 2 874 323 | 2/2006 |
| FR | 2 892 623 | 5/2007 |
| FR | 2 910 309 | 6/2008 |
| FR | 2 911 499 | 7/2008 |
| FR | 2 912 903 | 8/2008 |
| FR | 2 912 904 | 8/2008 |
| FR | 2 912 906 | 8/2008 |
| FR | 2 915 886 | 11/2008 |
| FR | 2 919 499 | 2/2009 |
| FR | 2 925 304 | 6/2009 |
| FR | 2 925 307 | 6/2009 |
| FR | 2 925 308 | 6/2009 |
| FR | 2 925 309 | 6/2009 |
| FR | 2 925 311 | 6/2009 |
| GB | 1 288 128 | 9/1972 |
| GB | 2 003 938 | 3/1979 |
| GB | 1 554 331 | 10/1979 |
| GB | 2 065 177 | 6/1981 |
| GB | 2 142 348 | 1/1985 |
| GB | 2 170 830 | 8/1986 |
| GB | 2 188 948 | 10/1987 |
| GB | 2 217 735 | 11/1989 |
| JP | 58-035106 | 3/1983 |
| JP | 59-106413 | 6/1984 |
| JP | 1-165514 | 6/1989 |
| JP | 10-101537 | 4/1998 |
| JP | 2001-233748 | 8/2001 |
| JP | 2001-302471 | 10/2001 |
| JP | 2003-095984 | 4/2003 |
| JP | 2003-238370 | 8/2003 |
| JP | 2004-262886 | 9/2004 |
| JP | 2006-282524 | 10/2006 |
| JP | 2008-074705 | 4/2008 |
| WO | WO 91/11985 | 8/1991 |
| WO | WO 97/01323 | 1/1997 |
| WO | WO 97/04739 | 2/1997 |
| WO | WO 97/12587 | 4/1997 |
| WO | WO 98/03150 | 1/1998 |
| WO | WO 01/28508 | 4/2001 |
| WO | WO 01/41723 | 6/2001 |
| WO | WO 01/43709 | 6/2001 |
| WO | WO 01/60327 | 8/2001 |
| WO | WO 02/089748 | 11/2002 |
| WO | WO 03/053329 | 7/2003 |
| WO | WO 03/084495 | 10/2003 |

| | | |
|---|---|---|
| WO | WO 2005/025525 | 3/2005 |
| WO | WO 2005/055966 | 6/2005 |
| WO | WO 2006/026851 | 3/2006 |
| WO | WO 2007/006418 | 1/2007 |
| WO | WO 2007/096027 | 8/2007 |
| WO | WO 2008/021641 | 2/2008 |
| WO | WO 2008/096497 | 8/2008 |
| WO | WO 2009/080667 | 7/2009 |
| WO | WO 2009/080668 | 7/2009 |
| WO | WO 2009/080669 | 7/2009 |
| WO | WO 2009/080670 | 7/2009 |

OTHER PUBLICATIONS

Copending U.S. Appl. No. 12/642,568, filed Dec. 18, 2009.
Copending U.S. Appl. No. 12/642,575, filed Dec. 18, 2009.
Copending U.S. Appl. No. 12/642,583, filed Dec. 18, 2009.
Copending U.S. Appl. No. 12/642,592, filed Dec. 18, 2009.
Copending U.S. Appl. No. 12/642,593, filed Dec. 18, 2009.
Copending U.S. Appl. No. 12/642,599, filed Dec. 18, 2009.
Copending U.S. Appl. No. 12/642,624, filed Dec. 18, 2009.
Copending U.S. Appl. No. 12/642,637, filed Dec. 18, 2009.
Copending U.S. Appl. No. 12/809,140, filed Jun. 18, 2010.
English language Abstract of DE 10 2005 011 459, dated Sep. 14, 2006.
English language Abstract of DE 10 2005 032 798, dated Jan. 25, 2007.
English language Abstract of DE 10 2005 059 647, dated Jun. 14, 2007.
English language Abstract of DE 10 2006 012 575, dated Feb. 8, 2007.
English language Abstract of DE 10 2006 020 050, dated Oct. 31, 2007.
English language Abstract of DE 10 2006 061 830, dated Jun. 26, 2008.
English language abstract of DE 100 28 723, dated Dec. 20, 2001.
English language Abstract of DE 100 56 266, dated May 23, 2002.
English language Abstract of DE 101 48 571, dated Apr. 24, 2003.
English language Abstract of DE 101 48 671, dated Apr. 10, 2003.
English language Abstract of DE 195 27 121, dated Jan. 30, 1997.
English language Abstract of DE 197 12 980, dated Oct. 1, 1998.
English language Abstract of DE 197 23 538, dated Sep. 17, 1998.
English language Abstract of DE 199 62 869, dated Jun. 28, 2001.
English language Abstract of DE 20 05 076, dated Aug. 6, 1970.
English language Abstract of DE 38 14 356, dated Sep. 8, 1988.
English language Abstract of DE 43 09 509, dated Sep. 29, 1994.
English language Abstract of EP 1 023 891 dated Oct. 10, 2001.
English language Abstract of EP 1 166 749, dated Jan. 2, 2002.
English language Abstract of EP 1 321 132, dated Jun. 25, 2003.
English language Abstract of EP 1 568 354, dated Aug. 31, 2005.
English language Abstract of EP 1 716 840, dated Nov. 2, 2006.
English language Abstract of EP 1 862 198, dated Dec. 5, 2007.
English language Abstract of EP 2 005 939, dated Dec. 24, 2008.
English language Abstract of EP 2 018 848, dated Jan. 28, 2009.
English language Abstract of FR 2 616 324, dated Dec. 16, 1988.
English language Abstract of FR 2 779 949, dated Dec. 24, 1999.
English language Abstract of FR 2 842 101, dated Jan. 16, 2004.
English language Abstract of FR 2 870 724, dated Dec. 2, 2005.
English language Abstract of FR 2 892 623, dated May 4, 2007.
English language Abstract of FR 2 910 309, dated Jun. 27, 2008.
English language Abstract of FR 2 911 499, dated Jul. 25, 2008.
English language Abstract of FR 2 912 903, dated Aug. 29, 2008.
English language Abstract of FR 2 912 904, dated Aug. 29, 2008.
English language Abstract of FR 2 912 906, dated Aug. 29, 2008.
English language Abstract of FR 2 915 886, dated Nov. 14, 2008.
English language Abstract of FR 2 919 499, dated Feb. 6, 2009.
English language Abstract of FR 2 925 304, dated Jun. 26, 2009.
English language Abstract of FR 2 925 308, dated Jun. 26, 2009.
English language Abstract of FR 2 925 309, dated Jun. 26, 2009.
English language Abstract of JP 1-165514, dated Jun. 29, 1989.
English language Abstract of JP 2001-233748, dated Aug. 28, 2001.
English language Abstract of JP 2001-302471, dated Oct. 31, 2001.
English language Abstract of JP 2003-095984, dated Apr. 3, 2003.
English language Abstract of JP 2003-238370, dated Aug. 27, 2003.
English language Abstract of JP 2004-262886, dated Sep. 24, 2004.
English language Abstract of JP 2006-282524, dated Oct. 19, 2006.
English language Abstract of JP 2008-074705, dated Apr. 3, 2008.
English language Abstract of JP 58-035106, dated Mar. 1, 1983.
English language Abstract of JP 59-106413, dated Jun. 20, 1984.
English language Abstract of WO 2007/096027, dated Aug. 30, 2007.
English language Abstract of WO 2008/096497, dated Aug. 14, 2008.
English language Abstract of WO 91/11985, dated Aug. 22, 1991.
English language Abstract of WO 97/04739, dated Feb. 13, 1997.
European Search Report for EP 08 17 2444, dated Apr. 13, 2009.
European Search Report for EP 08 17 2449, dated Apr. 13, 2009.
European Search Report for EP 08 17 2454, dated Apr. 3, 2009.
European Search Report for EP 09 17 9779, dated May 5, 2010.
European Search Report for EP 09 17 9789, dated Feb. 19, 2010.
European Search Report for EP 09 17 9844, dated Apr. 22, 2010.
European Search Report for EP 09 17 9884, dated Feb. 24, 2010.
European Search Report for EP 09 17 9885, dated Feb. 25, 2010.
European Search Report for EP 09 17 9887, dated Feb. 25, 2010.
European Search Report for EP 09 17 9888, dated Mar. 24, 2010.
European Search Report for EP 09 17 9892, dated Apr. 8, 2010.
European Search Report for EP 09 17 9895, dated Feb. 23, 2010.
European Search Report for EP 09 17 9899, dated Mar. 17, 2010.
European Search Report for EP 09 17 9911, dated Apr. 26, 2010.
European Search Report for EP 09 17 9914, dated Mar. 25, 2010.
European Search Report for EP 09 17 9992, dated Mar. 24, 2010.
European Search Report for EP 09 18 0003, dated Feb. 24, 2010.
French Search Report for FR 07/60273, dated Aug. 20, 2008.
French Search Report for FR 07/60274, dated Aug. 20, 2008.
French Search Report for FR 07/60278, dated Aug. 20, 2008.
French Search Report for FR 08/07283, dated Sep. 30, 2009.
French Search Report for FR 08/07285, dated Sep. 28, 2009.
French Search Report for FR 08/07286, dated Sep. 24, 2009.
French Search Report for FR 08/07287, dated Oct. 13, 2009.
French Search Report for FR 08/07288, dated Nov. 4, 2009.
French Search Report for FR 08/07290, dated Oct. 14, 2009.
French Search Report for FR 08/07291, dated Oct. 19, 2009.
French Search Report for FR 08/07292, dated Aug. 25, 2009.
French Search Report for FR 08/07294, dated Aug. 19, 2009.
French Search Report for FR 08/07298, dated Nov. 2, 2009.
French Search Report for FR 08/07304, dated Oct. 1, 2009.
French Search Report for FR 08/07306, dated Aug. 13, 2009.
French Search Report for FR 08/07307, dated Aug. 24, 2009.
French Search Report for FR 08/07309, dated Aug. 3, 2009.
French Search Report for FR 08/07310, dated Oct. 2, 2009.
French Search Report for FR 08/07312, dated Oct. 1, 2009.
French Search Report for FR 08/07313, dated Aug. 26, 2009.
French Search Report for FR 08/07314, dated Aug. 27, 2009.
French Search Report for FR 08/07315, dated Nov. 11, 2009.
French Search Report for FR 08/07316, dated Nov. 18, 2009.
French Search Report for FR 08/07319, dated Aug. 3, 2009.
French Search Report for FR 08/07320, dated Sep. 15, 2009.
French Search Report for FR 08/07321, dated Aug. 5, 2009.
French Search Report for FR 08/07322, dated Sep. 24, 2009.
French Search Report for FR 08/07323, dated Sep. 24, 2009.
French Search Report for FR 08/58838, dated Sep. 3, 2009.
French Search Report for FR 08/58840, dated Sep. 30, 2009.
French Search Report for FR 08/58880, dated Sep. 18, 2009.
French Search Report for FR 08/58881, dated Sep. 29, 2009.
French Search Report for FR 08/58886, dated Nov. 3, 2009.
French Search Report for FR 08/58888, dated Nov. 3, 2009.
French Search Report for FR 08/58889, dated Sep. 30, 2009.
French Search Report for FR 08/58890, dated Sep. 21, 2009.
French Search Report for FR 08/58891, dated Aug. 24, 2009.
French Search Report for FR 08/58892, dated Sep. 24, 2009.
French Search Report for FR 09/51367, dated Jan. 29, 2010.
French Search Report for FR 09/54264, dated Mar. 5, 2010.
French Search Report for FR 09/56389, dated Jun. 14, 2010.
French Search Report for FR 09/57176, dated Jun. 17, 2010.
International Search Report for PCT/FR2009/052617, dated Mar. 30, 2010.
Notice of Allowance mailed Aug. 26, 2010, in U.S. Appl. No. 12/642,624.
Notice of Allowance mailed Aug. 26, 2010, in U.S. Appl. No. 12/642,637.

Notice of Allowance mailed Aug. 27, 2010, in U.S. Appl. No. 12/642,513.
Notice of Allowance mailed in co-pending U.S. Appl. No. 12/339,753, dated Jul. 9, 2010.
Notice of Allowance mailed Jun. 11, 2010, in U.S. Appl. No. 12/642,489.
Notice of Allowance mailed Sep. 16, 2010, in U.S. Appl. No. 12/642,480.
Notice of Allowance mailed Sep. 16, 2010, in U.S. Appl. No. 12/642,555.
Notice of Allowance mailed Sep. 21, 2010, in U.S. Appl. No. 12/642,489.
Notice of Allowance mailed Sep. 22, 2010, in U.S. Appl. No. 12/642,551.
Notice of Allowance mailed Sep. 23, 2010, in U.S. Appl. No. 12/642,536.
Notice of Allowance mailed Sep. 7, 2010, in U.S. Appl. No. 12/642,599.
Notice of Allowance mailed Sep. 8, 2010, in U.S. Appl. No. 12/642,543.
Notice of Allowance mailed Sep. 9, 2010, in U.S. Appl. No. 12/642,531.
Office Action mailed Aug. 11, 2010, in co-pending U.S. Appl. No. 12/642,593.
Office Action mailed Aug. 26, 2010, in co-pending U.S. Appl. No. 12/642,473.
Office Action mailed Feb. 1, 2010, in co-pending U.S. Appl. No. 12/339,753.
Office Action mailed Sep. 17, 2010, in co-pending U.S. Appl. No. 12/642,506.
Office Action mailed Sep. 21, 2010, in co-pending U.S. Appl. No. 12/642,468.
Office Action mailed Sep. 22, 2010, in co-pending U.S. Appl. No. 12/642,492.
Office Action mailed Sep. 3, 2010, in co-pending U.S. Appl. No. 12/642,451.
STIC Search Report for U.S. Appl. No. 12/642,492, dated Jul. 14, 2010.

* cited by examiner

METHOD FOR DYEING IN THE PRESENCE OF AT LEAST ONE OXIDIZING AGENT AND AT LEAST ONE ORGANIC AMINE, DEVICE FOR USE THEREOF AND READY-TO-USE COMPOSITION

This application claims benefit of U.S. Provisional Application No. 61/006,483, filed Jan. 16, 2008, the contents of which are incorporated herein by reference. This application also claims benefit of priority under 35 U.S.C. §119 to French Patent Application No. FR 0760277, filed Dec. 21, 2007, the contents of which are also incorporated herein by reference.

Disclosed herein is a process for dyeing human keratin fibers in the presence of at least one oxidizing agent, comprising the use of: at least one anhydrous composition (A) comprising at least one fatty substance, at least one organic amine having a pKb less than 12 at 25° C., and at least one surfactant, at least one oxidizing composition (B), and at least one composition (C) comprising at least one dye.

Also disclosed herein is a multi-compartment device or kit, comprising at least one first compartment containing the abovementioned at least one anhydrous composition (A), at least one second compartment comprising the at least one oxidizing composition (B), and at least one third compartment comprising the at least one composition (C) comprising at least one dye.

Still further disclosed herein is a ready-to-use composition for dyeing human keratin fibers, comprising at least 35% by weight of at least one abovementioned fatty substance, at least one abovementioned organic amine, at least one above-mentioned surfactant, at least one abovementioned dye, and at least one abovementioned oxidizing agent.

Among the methods for dyeing human keratin fibers, such as the hair, non-limiting mention may be made of oxidation dyeing or permanent dyeing. For example, those dyeing methods use at least one oxidation dye precursor, and usually at least one oxidation base optionally combined with at least one coupler.

In general, oxidation bases can be chosen from ortho- or para-phenylenediamines, ortho- or para-aminophenols, and heterocyclic compounds. These oxidation bases are colorless or weakly colored compounds, which, when combined with oxidizing products, can give access to colored species via a process of oxidative condensation.

The shades obtained with these oxidation bases are often varied by combining them with at least one coupler, these couplers being chosen, for example, from aromatic meta-diamines, meta-aminophenols, meta-diphenols, and certain heterocyclic compounds, such as indole compounds.

The variety of molecules used as oxidation bases and couplers can allow a wide range of colors to be obtained.

Direct dyeing or semi-permanent dyeing is also known. The process conventionally used in direct dyeing involves applying to the keratin fibers direct dyes, which are colored and coloring molecules that have affinity for the fibers, leaving them on for a time to allow the molecules to penetrate, by diffusion, into the fiber, and in rinsing them off.

The direct dyes frequently used are, for example, chosen from nitrobenzene, anthraquinone, nitropyridine, azo, methine, azomethine, xanthene, acridine, azine, and triarylmethane direct dyes.

This type of process does not generally involve the use of an oxidizing agent to develop the coloration. However, it is possible to use one in order to obtain, along with the coloration, a lightening effect. Such a process is then referred to as direct dyeing or semi-permanent dyeing under lightening conditions.

Processes of permanent or semi-permanent dyeing under lightening conditions thus may involve using, for example, along with the dye composition, an aqueous composition comprising at least one oxidizing agent, under alkaline pH conditions in the majority of cases. This at least one oxidizing agent can degrade the melanin of the hair, which, depending on the nature of the oxidizing agent present, may lead to a more or less pronounced lightening of the fibers. Thus, for relatively weak lightening, the at least one oxidizing agent may be, for example, hydrogen peroxide. When more substantial lightening is desired, peroxygenated salts, such as persulfates, may be used in the presence of hydrogen peroxide.

At least one difficulty may arise from the fact that these processes are often performed under alkaline conditions and that the alkaline agent most commonly used is aqueous ammonia. Aqueous ammonia is frequently used in processes of this type. The reason for this is that it may allow the pH of the composition to be adjusted to an alkaline pH to enable activation of the oxidizing agent. In addition, this agent may also cause swelling of the keratin fiber, with opening of the scales, which can promote the penetration of the oxidizing agent, and also of the dyes, for example the oxidation dyes, into the fiber, and thus can increase the efficacy of the dyeing reaction.

However, this basifying agent can be very volatile, which users may find disagreeable due to the characteristic strong, rather unpleasant odor of ammonia that is given off during the process.

Furthermore, the amount of ammonia given off may require the use of higher amounts than necessary in order to compensate for this loss. This may affect the user, who not only may remain inconvenienced by the odor, but may also be confronted with greater risks of intolerance, for instance irritation of the scalp, such as stinging.

The option of replacing all or at least some of the aqueous ammonia with at least one other standard basifying agent frequently does not lead to compositions that can be as efficient as those based on aqueous ammonia, for example, since those basifying agents do not always afford sufficient lightening of pigmented fibers in the presence of an oxidizing agent.

Thus, there is a need in the art for dyeing processes performed in the presence of at least one oxidizing agent, which do not have at least one of the drawbacks of those associated with existing processes, due to the presence of large amounts of aqueous ammonia, while at the same time maintaining at least some of the efficiency, with respect to the dyeing power obtained, the chromaticity and the homogeneity of the coloration along the fiber.

For instance, the process according to the present disclosure leads to strong colorations that can allow gray hair to be covered.

Accordingly, one aspect of the present disclosure is a process for dyeing human keratin fibers in the presence of at least one oxidizing agent comprising applying to the fibers
  at least one anhydrous composition (A) comprising at least one fatty substance, at least one organic amine having a pKb less than 12 at 25° C., and at least one surfactant;
  at least one composition (B) comprising at least one oxidizing agent; and
  at least one composition (C) comprising at least one dye chosen from oxidation dyes and direct dyes.

The present disclosure also relates to a multi-compartment device or kit comprising at least one first compartment containing at least one anhydrous composition (A) comprising at least one fatty substance, at least one organic amine having a pKb less than 12 at 25° C., and at least one surfactant, at least one second compartment containing at least one composition (B) comprising at least one oxidizing agent, and at least one third compartment containing at least one composition (C) comprising at least one dye chosen from oxidation dyes and direct dyes.

The present disclosure further relates to a ready-to-use composition for dyeing human keratin fibers, comprising at least 35% by weight of at least one fatty substance, at least one organic amine having a pKb less than 12 at 25° C., at least one surfactant, at least one dye chosen from oxidation dyes and direct dyes, and at least one oxidizing agent.

At least one other characteristic and benefit of the present disclosure may emerge more clearly upon reading the description and the non-limiting examples that follow.

In the text of the present disclosure, unless otherwise indicated, the limits of a range of values are included in that range.

The human keratin fibers treated by the process according to the present disclosure include hair.

The dyeing process may be performed, for example, in the presence of an anhydrous composition (A).

As used herein, the term "anhydrous composition" means a composition with a water content of less than 5% by weight, for example less than or equal to 2% by weight, such as less than or equal to 1% by weight relative to the weight of the composition. The water may, for example, be in the form of bound water, such as the water of crystallization of salts, or traces of water absorbed by the starting materials used in the preparation of the compositions according to the present disclosure.

As mentioned above, the at least one anhydrous composition (A) according to the present disclosure comprises at least one fatty substance.

As used herein, the term "fatty substance" means an organic compound that is insoluble in water at ordinary temperature (25° C.) and at atmospheric pressure (760 mmHg) (solubility of less than 5%, for example less than 1% and further for example less than 0.1%). In addition, the at least one fatty substance is soluble in organic solvents under the same temperature and pressure conditions, for instance chloroform, ethanol, or benzene.

According to the present disclosure, the at least one fatty substance can be chosen from compounds that are liquid or pasty at room temperature and at atmospheric pressure.

By way of non-limiting example, the at least one fatty substance can be chosen from alkanes, fatty alcohols, fatty acids, fatty acid esters, fatty alcohol esters, mineral oils, plant oils, animal oils, synthetic oils, silicones, and waxes.

For the purposes of the present disclosure, the fatty alcohols, fatty esters, and fatty acids may comprise at least group chosen from linear and branched, saturated and unsaturated hydrocarbon-based groups comprising 6 to 30 carbon atoms, optionally substituted, for example, with at least one hydroxyl group (for example 1 to 4). If they are unsaturated, these compounds may comprise one to three conjugated or nonconjugated carbon-carbon double bonds.

As regards alkanes, these alkanes, comprising from 6 to 30 carbon atoms, can be linear. Non-limiting mention may be made of hexane and dodecane.

As oils that may be used in the at least one anhydrous composition (A) of the present disclosure, non-limiting examples that may be mentioned include:
  hydrocarbon-based oils of animal origin, such as perhydrosqualene;
  hydrocarbon-based oils of plant origin, such as liquid fatty acid triglycerides comprising from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names MIGLYOL® 810, 812, and 818 by the company Dynamit Nobel, jojoba oil, and shea butter oil;
  linear or branched hydrocarbons of mineral or synthetic origin, such as volatile or nonvolatile liquid paraffins, and derivatives thereof, petroleum jelly, liquid petroleum jelly, polydecenes, hydrogenated polyisobutene such as PARLEAM®, isoparaffins, for instance isohexadecane, and isodecane;
  linear or branched, saturated or unsaturated fatty alcohols comprising from 8 to 30 carbon atoms, for instance cetyl alcohol, stearyl alcohol, and the mixture thereof (cetylstearyl alcohol), octyidodecanol, 2-butyloctanol, 2-hexyldecanol, 2-undecylpentadecanol, oleyl alcohol, or linoleyl alcohol;
  partially hydrocarbon-based and/or silicone-based fluoro oils, for instance those described in Japan Patent Application No. JP-A-2-295 912; fluoro oils that may also be mentioned by way of non-limiting example include perfluoromethylcyclopentane and perfluoro-1,3-dimethylcyclohexane, sold under the names FLUTEC® PC1 and FLUTEC® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name FORALKYL® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The at least one wax can, by way of non-limiting example, be chosen from carnauba wax, candelilla wax, esparto grass wax, paraffin wax, ozokerites, plant waxes such as olive wax, rice wax, hydrogenated jojoba wax, and or the absolute waxes of flowers such as the essential wax of blackcurrant blossom sold by the company Bertin (France), animal waxes, for instance beeswaxes and modified beeswaxes (cerabellina); other waxes or waxy starting materials that may be used according to the present disclosure include marine waxes such as the product sold by the company Sophim under the reference M82, and polyethylene waxes, and polyolefin waxes in general.

The at least one fatty acid may, by way of non-limiting example, be saturated or unsaturated and comprise from 6 to 30 carbon atoms, for example from 9 to 30 carbon atoms. Further by way of non-limiting example, the at least one fatty acid can be chosen from myristic acid, palmitic acid, stearic acid, behenic acid, oleic acid, linoleic acid, linolenic acid, and isostearic acid.

The esters are chosen from esters of saturated and unsaturated, linear and branched $C_1$-$C_{26}$ aliphatic mono- and polyacids and of saturated and unsaturated, linear and branched $C_1$-$C_{26}$ aliphatic mono- and polyalcohols, the total carbon number of the esters being greater than or equal to 10.

Among the monoesters, non-limiting mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl, or stearyl myristate, hexyl stearate, butyl stearate, isobutyl stearate; dioctyl malate, hexyl laurate, and 2-hexyldecyl laurate.

By way of further non-limiting example, esters chosen from esters of $C_4$-$C_{22}$ dicarboxylic and tricarboxylic acids, esters of $C_1$-$C_{22}$ alcohols esters of mono-, di-, and tricarboxylic acids and esters of $C_2$-$C_{26}$ di-, tri-, tetra-, and pentahydroxy alcohols may also be used.

Non-limiting mention of the following may also be made: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Further among the esters that may be used in the at least one anhydrous composition (A) according to the present disclosure, non-limiting mention may be made of ethyl, isopropyl, myristyl, cetyl, or stearyl palmitate, 2-ethylhexyl palmitate, 2-octyldecyl palmitate, alkyl myristates such as isopropyl, butyl, cetyl, or 2-octyldodecyl myristate, hexyl stearate, butyl stearate, isobutyl stearate, dioctyl malate, hexyl laurate, 2-hexyldecyl laurate, isononyl isononanoate, or cetyl octanoate.

The at least one fatty substance may also comprise, as fatty ester, sugar esters and diesters of $C_6$-$C_{30}$, for example $C_{12}$-$C_{22}$ fatty acids. As used herein, the term "sugar" means oxygen-bearing hydrocarbon-based compounds comprising several alcohol functional groups, with or without aldehyde or ketone functional groups, and which comprise at least 4 carbon atoms. These sugars may be monosaccharides, oligosaccharides, or polysaccharides.

Non-limiting examples of suitable sugars that may be mentioned include sucrose (or saccharose), glucose, galactose, ribose, fructose, maltose, mannose, arabinose, xylose and lactose, and derivatives thereof, for example alkyl derivatives, such as methyl derivatives, for instance methylglucose.

For example, the sugar esters of fatty acids may be chosen from esters or mixtures of esters of sugars described previously and of linear and branched, saturated and unsaturated $C_6$-$C_{30}$, for example $C_{12}$-$C_{22}$ fatty acids. If they are unsaturated, these compounds may comprise one to three conjugated or nonconjugated carbon-carbon double bonds.

By way of further non-limiting example, the esters according to the present disclosure may also be chosen from mono-, di-, tri-, tetraesters, and polyesters, and mixtures thereof.

These esters may be chosen, by way of non-limiting example, from oleates, laurates, palmitates, myristates, behenates, cocoates, stearates, linoleates, linolenates, caprates, and arachidonates, and mixtures thereof such as, oleo-palmitate, oleo-stearate, and palmito-stearate mixed esters.

In at least one embodiment, monoesters or diesters are used, for instance sucrose, glucose, and methylglucose, mono- or dioleates, stearates, behenates, oleopalmitates, linoleates, linolenates, and oleostearates.

Non-limiting mention may be made of the product sold under the name GLUCATE® DO by the company Amerchol, which is a methylglucose dioleate.

Non-limiting examples of esters or mixtures of esters of sugar, and of fatty acid that may also be mentioned include:

the products sold under the names F160, F140, F110, F90, F70, and SL40 by the company Crodesta, which are, respectively, denoting sucrose palmitostearates formed from 73% monoester and 27% diester and triester, from 61% monoester and 39% diester, triester, and tetraester, from 52% monoester and 48% diester, triester, and tetraester, from 45% monoester and 55% diester, triester, and tetraester, from 39% monoester and 61% diester, triester, and tetraester, and sucrose monolaurate;

the products sold under the name Ryoto Sugar Esters, for example B370, which is sucrose behenate formed from 20% monoester and 80% di-triester-polyester;

the sucrose mono-dipalmito-stearate sold by the company Goldschmidt under the name TEGOSOFT® PSE.

The silicones that may be used in the at least one anhydrous composition (A) of the present disclosure include volatile, nonvolatile, cyclic, linear, and branched silicones, which are unmodified or modified with organic groups, having a viscosity ranging from $5 \times 10^{-6}$ to 2.5 $m^2$/s at 25° C., for example ranging from $1 \times 10^{-5}$ to 1 $m^2$/s.

The silicones that may be used in accordance with the present disclosure may, by way of non-limiting example, be in the form of oils, waxes, resins, and gums.

By way of further non-limiting example, the at least one silicone may be chosen from polydialkylsiloxanes, for example polydimethylsiloxanes (PDMS), and organomodified polysiloxanes comprising at least one functional group chosen from poly(oxyalkylene) groups, amino groups, and alkoxy groups.

The organopolysiloxanes are defined in greater detail in Walter Noll's "Chemistry and Technology of Silicones" (1968) Academic Press. They can be volatile or nonvolatile.

When they are volatile, the silicones may, for example, be chosen from those having a boiling point ranging from 60° C. to 260° C., and further for example from:

(i) cyclic polydialkylsiloxanes comprising from 3 to 7 silicon atoms, for example from 4 to 5 silicon atoms. These are, for example, octamethylcyclotetrasiloxane sold further for example under the name VOLATILE SILICONE® 7207 by Union Carbide or SILBIONE® 70045 V 2 by Rhodia, decamethylcyclopentasiloxane sold under the name VOLATILE SILICONE® 7158 by Union Carbide, and SILBIONE® 70045 V 5 by Rhodia, and mixtures thereof.

Non-limiting mention may also be made of cyclocopolymers of the dimethylsiloxane/methylalkylsiloxane type, such as VOLATILE SILICONE® FZ 3109 sold by the company Union Carbide, of the formula:

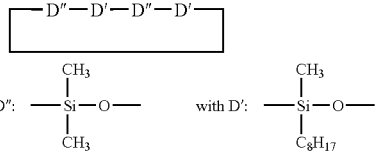

Non-limiting mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes comprising 2 to 9 silicon atoms and having a viscosity of less than or equal to $5 \times 10^{-6}$ m$^2$/s at 25° C. A non-limiting example is decamethyltetrasiloxane sold, for example under the name SH 200 by the company Toray Silicone. Silicones belonging to this category are also described in the article published in Cosmetics and Toiletries, Vol. 91, Jan. 76, pp. 27-32, Todd & Byers "Volatile Silicone Fluids for Cosmetics".

By way of non-limiting example, nonvolatile polydialkylsiloxanes, polydialkylsiloxane gums and resins, polyorganosiloxanes modified with organofunctional groups above, and mixtures thereof, may be used in the at least one anhydrous composition (A) according to the present disclosure.

By way of further non-limiting example, polydialkylsiloxanes, including polydimethylsiloxanes comprising trimethylsilyl end groups may be used.

The viscosity of the silicones is measured, for example, at 25° C. according to ASTM standard 445 Appendix C.

Among these polydialkylsiloxanes, non-limiting mention may be made of the following commercial products:
the SILBIONE® oils of the 47 and 70 047 series or the MIRASIL® oils sold by Rhodia, for instance the oil 70 047 V 500 000;
the oils of the MIRASIL® series sold by the company Rhodia;
the oils of the 200 series from the company Dow Corning, such as DC200 with a viscosity of 60,000 mm$^2$/s;
the VISCASIL® oils from General Electric and certain oils of the SF series (SF 96, SF 18) from General Electric.

Non-limiting mention may also be made of polydimethylsiloxanes comprising dimethylsilanol end groups known under the name Dimethiconol (CTFA), such as the oils of the 48 series from the company Rhodia.

In this category of polydialkylsiloxanes, non-limiting mention may also be made of the products sold under the names ABIL WAX® 9800 and 9801 by the company Goldschmidt, which are poly($C_1$-$C_{20}$)dialkylsiloxanes.

The silicone gums that can be used in the at least one anhydrous composition (A) in accordance with the present disclosure may, by way of non-limiting example, be polydialkylsiloxanes, for example polydimethylsiloxanes with high number-average molecular masses ranging from 200,000 to 1,000,000, used alone or as a mixture in a solvent. This solvent may, by way of non-limiting example, be chosen from volatile silicones, polydimethylsiloxane (PDMS) oils, polyphenylmethylsiloxane (PPMS) oils, isoparaffins, polyisobutylenes, methylene chloride, pentane, dodecane, and tridecane, and mixtures thereof.

By way of further non-limiting example, mixtures that can be used in accordance with the present disclosure include mixtures such as
mixtures formed from a polydimethylsiloxane hydroxylated at the chain end, and dimethiconol (CTFA) and from a cyclic polydimethylsiloxane also known as cyclomethicone (CTFA), such as the product Q2 1401 sold by the company Dow Corning;
mixtures formed from a polydimethylsiloxane gum with a cyclic silicone, such as the product SF 1214 SILICONE FLUID from the company General Electric; this product is an SF 30 gum corresponding to a dimethicone, having a number-average molecular weight of 500,000, dissolved in the oil SF 1202 SILICONE FLUID corresponding to decamethylcyclopentasiloxane; and
mixtures of two PDMSs with different viscosities, for example a PDMS gum and a PDMS oil, such as the product SF 1236 from the company General Electric. The product SF 1236 is a mixture of an SE 30 gum defined above, having a viscosity of 20 m$^2$/s, and an SF 96 oil, with a viscosity of $5 \times 10^{-6}$ m$^2$/s. This product, for example, comprises 15% SE 30 gum and 85% SF 96 oil.

The organopolysiloxane resins that can be used in accordance with the present disclosure may, by way of non-limiting example, be crosslinked siloxane systems comprising the following units:

$$(R)_2SiO_{2/2}, (R)_3SiO_{1/2}, RSiO_{3/2}, \text{ and } SiO_{4/2}$$

wherein R is independently chosen from a hydrocarbon-based group comprising 1 to 16 carbon atoms. For example R may be a $C_1$-$C_4$ lower alkyl radical, for example methyl.

Among these resins, non-limiting mention may be made of the product sold under the name DOW CORNING 593 and those sold under the names SILICONE FLUID SS 4230 and SS 4267 by the company General Electric, which are silicones of dimethyl/trimethyl siloxane structure.

Non-limiting mention may also be made of the trimethyl siloxysilicate type resins sold, for example, under the names X22-4914, X21-5034, and X21-5037 by the company Shin-Etsu.

The organomodified silicones that can be used in accordance with the present disclosure may, by way of non-limiting example, be silicones as defined above and comprising in their structure at least one organofunctional group attached via a hydrocarbon-based radical.

Besides the silicones described above, the organomodified silicones may, by way of non-limiting example, be polydiarylsiloxanes, for example polydiphenylsiloxanes, and polyalkylarylsiloxanes functionalized with the at least one organofunctional group mentioned previously.

The polyalkylarylsiloxanes may be chosen, for example, from linear and branched polydimethyl/methylphenylsiloxanes and polydimethyl/diphenylsiloxanes with a viscosity ranging from $1 \times 10^{-5}$ to $5 \times 10^{-2}$ m$^2$/s at 25° C.

Among these polyalkylarylsiloxanes, non-limiting examples that may be mentioned include the products sold under the following names:
the SILBIONE® oils of the 70 641 series from Rhodia;
the oils of the RHODOURS® 70 633 and 763 series from Rhodia;
the oil DOW CORNING 556 COSMETIC GRADE FLUID from Dow Corning;
the silicones of the PK series from Bayer, such as the product PK20;
the silicones of the PN and PH series from Bayer, such as the products PN1000 and PH1000;
certain oils of the SF series from General Electric, such as SF 1023, SF 1 154, SF 1250, and SF 1265.

Among the organomodified silicones, non-limiting mention may be made of polyorganosiloxanes comprising:
polyethyleneoxy and/or polypropyleneoxy groups optionally comprising $C_6$-$C_{24}$ alkyl groups, such as the products known as dimethicone copolyol sold by the company Dow Corning under the name DC 1248 or the oils SILWET® L 722, L 7500, L 77, and L 711 by the company Union Carbide, and the ($C_{12}$)alkylmethicone copolyol sold by the company Dow Corning under the name Q2 5200;
substituted or unsubstituted amine groups, such as the products sold under the name GP 4 SILICONE FLUID and GP 7100 by the company Genesee, or the products sold under the names Q2 8220 and DOW CORNING 929 and 939 by the company Dow Corning. The substituted amine groups can be, for example, $C_1$-$C_4$ aminoalkyl groups;

alkoxylated groups such as the product sold under the name SILICONE COPOLYMER F-755 by SWS Silicones, and ABIL WAX® 2428, 2434, and 2440 by the company Goldschmidt.

For example, the at least one fatty substance may be a compound that is liquid at a temperature of 25° C. and at atmospheric pressure.

In at least one embodiment, the at least one fatty substance may be chosen from liquid petroleum jelly, polydecenes, and liquid esters, and mixtures thereof.

The at least one anhydrous composition (A) has at least one fatty substance present in an amount ranging from 10% to 99% by weight, for example ranging from 20% to 90% by weight, such as ranging from 25% to 80% by weight, relative to the weight of the at least one anhydrous composition (A).

The at least one anhydrous composition (A) may also comprise at least one organic amine having a pKb less than 12 at 25° C., for example less than 10, such as less than 6. The pKb corresponds to the function of highest basicity.

In at least one embodiment of the present disclosure, the at least one organic amine is at least partially miscible with the at least one fatty substance, at room temperature and atmospheric pressure. For example, the at least one organic amine is totally soluble at a temperature of 25° C. and at atmospheric pressure (760 mmHg) in the at least one fatty substance. For example, the at least one fatty substance and the at least one organic amine form a single phase at 25° C. and at atmospheric pressure.

According to at least one embodiment of the present disclosure, the at least one organic amine comprises one or two functional groups chosen from primary, secondary, and tertiary amine functional groups, and at least one group chosen from linear and branched $C_1$-$C_8$ alkyl groups bearing at least one hydroxyl radical.

Non-limiting examples of the at least one organic amine may be alkanolamines such as mono-, di-, or trialkanolamines, comprising at least one identical or different $C_1$-$C_4$ hydroxyalkyl radicals.

Among the compounds of this type non-limiting mention may be made of monoethanolamine, diethanolamine, triethanolamine, monoisopropanolamine, diisopropanolamine, N-dimethylaminoethanolamine, 2-amino-2-methyl-1-propanol, triiso-propanolamine, 2-amino-2-methyl-1,3-propanediol, 3-amino-1,2-propanediol, 3-dimethylamino-1,2-propanediol, and tris(hydroxymethylamino)methane.

The at least one organic amine can be chosen from those of formula:

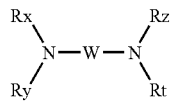

wherein W is chosen from $C_1$-$C_6$ alkylene residues optionally substituted with a hydroxyl group or a $C_1$-$C_6$ alkyl radical; Rx, Ry, Rz, and Rt, which may be identical or different, are chosen from a hydrogen atom and $C_1$-$C_6$ alkyl, $C_1$-$C_6$ hydroxyalkyl, and $C_1$-$C_6$ aminoalkyl radicals.

Non-limiting examples of such amines that may be mentioned include 1,3-diaminopropane, 1,3-diamino-2-propanol, spermine, and spermidine.

According to at least one aspect of the present disclosure, the at least one organic amine is chosen from at least one amino acid.

For example, the amino acids that may be used are of natural or synthetic origin, in L, D, or racemic form, and comprise at least one acid functional group chosen, for example, from carboxylic acid, sulfonic acid, phosphonic acid, and phosphoric acid functions. The at least one amino acid may be in its neutral or ionic form.

For example, the at least one amino acid can be an amino acid comprising an additional amine functional group optionally included in a ring or in a ureido functional group.

Such amino acids may, by way of non-limiting example, be chosen from those of formula (I):

wherein R is a group chosen from:

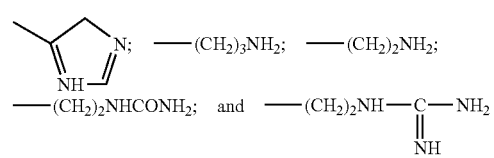

Non-limiting examples of the compounds corresponding to formula (I) include histidine, lysine, arginine, ornithine, and citrulline.

The at least one amino acid that may be used in the present disclosure include, by way of non-limiting example, aspartic acid, glutamic acid, alanine, arginine, ornithine, citrulline, asparagine, carnitine, cysteine, glutamine, lysine, histidine, lysine, isoleucine, leucine, methionine, N-phenylalanine, proline, serine, taurine, threonine, tryptophan, tyrosine, and valine.

In one aspect of the present disclosure, the at least one amino acid may be used as a mixture with at least one solid or pasty, for example pulverulent, adjuvant. The adjuvants may be chosen from clays, salts, anionic, nonionic, cationic, or zwitterionic surfactants, natural or synthetic thickeners, optionally modified starch, glass beads, silica, Nylon, alumina, titanium dioxide, zeolites, poly(methyl methacrylate) (PMMA), chitosan, maltodextrin, cyclodextrin, mono- or disaccharides, for instance glucose, sucrose, sorbitol, or fructose, zinc oxide, zirconium oxide, resin particles, for instance silicone or silica beads, talc, borosilicates, for example calcium borosilicate, polyethylene, cotton, polytetra-fluoroethylene (PTFE), cellulose and its derivatives, superabsorbent compounds, magnesium carbonate, calcium carbonate, corn seeds, polydimethylsiloxane gums, polyacrylamide, porous hydroxyapatite, silk, collagen, sawdust, wrack powder, crosslinked polyvinylpyrrolidone, calcium alginate, active charcoal, and poly(vinylidene chloride/acrylo-nitrile) particles, for example those sold under the general name EXPANCEL® by the company Akzo Nobel under the references EXPANCEL® WE, EXPANCEL® DE, and mixtures thereof.

According to at least one aspect of the present disclosure, the at least one organic amine is chosen from at least one amino acid. Non-limiting examples of the at least one amino acid that may be used include arginine, lysine, and histidine, and mixtures thereof.

According to at least one aspect of the present disclosure, the at least one organic amine can be chosen from at least one organic amine of heterocyclic type. Besides histidine that has already been mentioned in the amino acids, non-limiting mention may be made, for example, of pyridine, piperidine, imidazole, triazole, tetrazole, and benzimidazole.

According to at least one aspect of the present disclosure, the at least one organic amine can be chosen from at least one amino acid dipeptide. As amino acid dipeptides that may be used in the present disclosure, non-limiting mention may be made, for example, of carnosine, anserine, and baleine.

According to at least one aspect of the present disclosure, the at least one organic amine can be chosen from at least one compound comprising a guanidine functional group. As organic amines of this type that may be used in the present disclosure, besides arginine that has already been mentioned as an amino acid, non-limiting mention may be made of creatine, creatinine, 1,1-dimethylguanidine, 1,1-diethylguanidine, glycocyamine, metformin, agmatine, N-amidinoalanine, 3-guanidino-propionic acid, 4-guanidinobutyric acid, and 2-([amino(imino)methyl]amino)ethane-1-sulfonic acid.

For example, the at least one organic amine present in the at least one anhydrous composition (A) can be an alkanolamine. For instance, the at least one organic amine can be chosen from 2-amino-2-methyl-1-propanol and monoethanolamine. For example, the at least one organic amine can be monoethanolamine.

For example, the at least one anhydrous composition (A) has at least one organic amine present in an amount ranging from 0.1% to 40% by weight, for example from 0.5% to 20% by weight, relative to the weight of the composition.

The at least one anhydrous composition (A) also comprises at least one surfactant.

For example, the at least one surfactant can be chosen from nonionic surfactants and anionic surfactants.

By way of non-limiting example, the at least one anionic surfactant can be chosen from salts (such as alkali metal salts, for example sodium salts, ammonium salts, amine salts, amino alcohol salts, and alkaline-earth metal salts such as magnesium salts) of the following compounds:
  alkyl sulfates, alkyl ether sulfates, alkylamido ether sulfates, alkylaryl polyether sulfates, monoglyceride sulfates;
  alkylsulfonates, alkylamidesulfonates, alkylarylsulfonates, α-olefin sulfonates, paraffin sulfonates;
  alkyl phosphates, alkyl ether phosphates;
  alkylsulfosuccinates, alkyl ether sulfosuccinates, alkylamidesulfosuccinates;
  alkylsulfosuccinates;
  alkylsulfoacetates;
  acylsarcosinates; acylisethionates and N-acyltaurates;
  salts of fatty acids such as oleic acid, ricinoleic acid, palmitic acid, and stearic acid, coconut oil acid, and hydrogenated coconut oil acid;
  alkyl-D-galactoside uronic acid salts;
  acyllactylates;
  salts of polyoxyalkylenated alkyl ether carboxylic acids, of polyoxyalkylenated alkylaryl ether carboxylic acids, and of polyoxyalkylenated alkylamido ether carboxylic acids, for example those comprising from 2 to 50 ethylene oxide groups; and
  and mixtures thereof.

It should be noted that the alkyl or acyl radical of these various compounds can comprise from 6 to 24 carbon atoms, for example from 8 to 24 carbon atoms, and the aryl radical may, by way of non-limiting example, be chosen from phenyl and benzyl groups.

The at least one nonionic surfactant can be chosen, by way of non-limiting example, from monooxyalkylenated, polyoxyalkylenated, monoglycerolated, and polyglycerolated nonionic surfactants. The oxyalkylene units can, by way of non-limiting example, be oxyethylene and oxypropylene units, and a combination thereof, for instance oxyethylene units.

Non-limiting examples of oxyalkylenated nonionic surfactants that may be mentioned include:
  oxyalkylenated ($C_8$-$C_{24}$)alkylphenols,
  saturated or unsaturated, linear or branched, oxyalkylenated $C_8$-$C_{30}$ alcohols,
  saturated or unsaturated, linear or branched, oxyalkylenated $C_8$-$C_{30}$ amides,
  saturated or unsaturated, linear or branched, oxyalkylenated $C_8$-$C_{30}$ amines,
  esters of saturated or unsaturated, linear or branched, $C_8$-$C_{30}$ acids and of polyethylene
  glycols,
  polyoxyethylenated esters of saturated or unsaturated, linear or branched, $C_8$-$C_{30}$ acids and of sorbitol,
  saturated or unsaturated, oxyethylenated plant oils,
  condensates of ethylene oxide and/or of propylene oxide, alone or as mixtures.

The at least one surfactant comprises a number of moles of ethylene oxide and/or of propylene oxide ranging from 1 to 50, for example from 2 to 30. For example, the at least one nonionic surfactant may not comprise any oxypropylene units.

In accordance with at least one aspect of the present disclosure, the at least one oxyalkylenated nonionic surfactant may, by way of non-limiting example, be chosen from oxyethylenated $C_8$-$C_{30}$ alcohols and oxyethylenated $C_8$-$C_{30}$ amines.

As non-limiting examples of monoglycerolated and polyglycerolated nonionic surfactants, monoglycerolated and polyglycerolated $C_8$-$C_{40}$ alcohols can be used.

For example, the monoglycerolated and polyglycerolated $C_8$-$C_{40}$ alcohols can be chosen from those of formula:

$$RO\text{—}[CH_2\text{—}CH(CH_2OH)\text{—}O]_m\text{—}H$$

wherein R is chosen from linear and branched $C_8$-$C_{40}$ alkyl and alkenyl radicals, for example $C_8$-$C_{30}$ alkyl and alkenyl radical, and m is an integer ranging from 1 to 30, for example from 1 to 10.

As examples of compounds that are suitable in the context of the present disclosure, non-limiting mention may be made of lauryl alcohol comprising 4 mol of glycerol (INCI name: Polyglyceryl-4 Lauryl Ether), lauryl alcohol comprising 1.5 mol of glycerol, oleyl alcohol comprising 4 mol of glycerol (INCI name: Polyglyceryl-4 Oleyl Ether), oleyl alcohol comprising 2 mol of glycerol (INCI name: Polyglyceryl-2 Oleyl Ether), cetearyl alcohol comprising 2 mol of glycerol, cetearyl alcohol comprising 6 mol of glycerol, oleocetyl alcohol comprising 6 mol of glycerol, and octadecanol comprising 6 mol of glycerol.

The alcohol can be a mixture of alcohols in the same way that the value of m is a statistical value, which means that, in a commercial product, several species of polyglycerolated fatty alcohol may coexist in the form of a mixture.

Among the monoglycerolated and polyglycerolated alcohols, non-limiting examples include $C_8/C_{10}$ alcohol comprising 1 mol of glycerol, the $C_{10}/C_{12}$ alcohol comprising 1 mol of glycerol, and the $C_{12}$ alcohol comprising 1.5 mol of glycerol.

For example, the at least one surfactant present in the at least one anhydrous composition (A) can be a nonionic surfactant.

The at least one surfactant may be present in the at least one anhydrous composition (A) in an amount ranging, for example, from 0.1% to 50% by weight, further for example from 0.5% to 30% by weight, relative to the weight of the at least one anhydrous composition (A).

The at least one anhydrous composition (A) may also comprise various adjuvants conventionally used in hair dye compositions, such as anionic, cationic, nonionic, amphoteric, and zwitterionic polymers, and mixtures thereof; mineral thickeners, and fillers such as clays or talc; organic thickeners with, for example, anionic, cationic, nonionic, and amphoteric polymeric associative thickeners; antioxidants; penetrants; sequestrants; fragrances; dispersants; film-forming agents; ceramides; preserving agents; and opacifiers.

The above adjuvants may be present in an amount for each of them ranging, for example, from 0.01% to 20% by weight relative to the weight of the at least one anhydrous composition (A).

According to at least one aspect of the present disclosure, the at least one anhydrous composition (A) comprises at least one silica, for example of hydrophobic nature, for instance fumed silicas.

When present, the at least one silica is present in an amount ranging, for example, from 1% to 30% by weight relative to the weight of the at least one anhydrous composition (A).

For example, the at least one anhydrous composition (A) may be in the form of a gel or a cream.

As indicated previously, the process according to the present disclosure may be performed in the presence of at least one composition (B) comprising at least one oxidizing agent.

For example, the at least one oxidizing agent may be chosen from hydrogen peroxide, urea peroxide, alkali metal bromates and ferricyanides, and peroxygenated salts, for instance alkali metal and alkaline-earth metal persulfates, perborates and percarbonates, and peracids, and precursors thereof.

This at least one composition (B) may comprise, for example, hydrogen peroxide, such as an aqueous solution (aqueous hydrogen peroxide solution), the titre of which may range, for example, from 1 to 40 volumes, such as from 5 to 40 volumes.

As a function of the desired degree of lightening, the at least one composition (B) may also comprise an oxidizing agent chosen, for example, from peroxygenated salts.

Alternatively, in at least one embodiment, the at least one oxidizing agent may not be chosen from peroxygenated salts, peracids, and precursors thereof.

The at least one composition (B) may be aqueous or non-aqueous. As used herein, the term "aqueous composition" means a composition comprising more than 5% by weight of water, for example more than 10% by weight of water, such as more than 20% by weight of water.

For example, the at least one composition (B) may be an aqueous composition.

It may also comprise at least one organic solvent.

Non-limiting examples of organic solvents that may be mentioned include linear or branched $C_2$-$C_4$ alkanols, such as ethanol and isopropanol; glycerol; polyols and polyol ethers, for instance 2-butoxyethanol, propylene glycol, dipropylene glycol, propylene glycol monomethyl ether, diethylene glycol monomethyl ether, and monoethyl ether, and also aromatic alcohols, for instance benzyl alcohol and phenoxyethanol, and mixtures thereof.

When they are present, the at least one organic solvent is present in an amount ranging, for example, from 1% to 40% by weight, further for example from 5% to 30% by weight, relative to the weight of the at least one composition (B).

The at least one composition (B) may comprise at least one acidifying agent.

Non-limiting examples of the at least one acidifying agent include mineral and organic acids, for instance hydrochloric acid, orthophosphoric acid, sulfuric acid, carboxylic acids, for instance acetic acid, tartaric acid, citric acid, and lactic acid, and sulfonic acids.

The pH of the at least one composition (B), when it is aqueous, may be less than 7.

The at least one composition (B) may also comprise other ingredients conventionally used in the field, such as those detailed previously in the context of the at least one anhydrous composition (A).

Further, the at least one composition (B) may be in various forms, for instance solutions, emulsions, and gels.

The process according to the present disclosure is performed in the presence of at least one composition (C) comprising at least one dye chosen from oxidation dyes and direct dye.

The oxidation dyes are generally chosen from at least one oxidation base optionally combined with at least one coupler.

The at least one oxidation base may be chosen, by way of non-limiting example, from para-phenylenediamines, bis (phenyl)alkylenediamines, para-aminophenols, ortho-aminophenols, and heterocyclic bases, and the addition salts thereof.

Among the para-phenylenediamines of which non-limiting mention may be made are, for example, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methyl-aniline, N,N-bis(β-hydroxyethyl)-para-phenylenediamine, 4-N,N-bis(β-hydroxyethyl) amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, and the acid addition salts thereof.

Non-limiting examples among the para-phenylenediamines mentioned above include, para-phenylenediamine, para-tolylenediamine, 2-isopropyl-para-phenyl-enediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, and 2-β-acetylaminoethyloxy-para-phenylenediamine, and the acid addition salts thereof.

Among the bis(phenyl)alkylenediamines of which non-limiting mention may be made are, for example, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophen-yl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diamino-phenoxy)-3,6-dioxaoctane, and the addition salts thereof.

Among the para-aminophenols of which non-limiting mention may be made are, for example, para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and the acid addition salts thereof.

Among the ortho-aminophenols of which non-limiting mention may be made are, for example, 2-aminophenol, 2-amino-5-methylphenol, 2-amino-6-methylphenol, 5-acetamido-2-aminophenol, and the addition salts thereof.

Among the heterocyclic bases of which non-limiting mention may be made are, for example, pyridine derivatives, pyrimidine derivatives, and pyrazole derivatives.

Among the pyridine derivatives of which non-limiting mention may be made are the compounds described, for example, in Great Britain Patent Nos. GB 1 026 978 and GB 1 153 196, for instance 2,5-diaminopyridine, 2-(4-methoxyphenyl)amino-3-amino-pyridine, 3,4-diaminopyridine, and the addition salts thereof.

Other pyridine oxidation bases that may be used in the present disclosure are, for example, the 3-aminopyrazolo[1,5-a]pyridine oxidation bases and addition salts thereof described, for example, in French Patent Application No. FR 2 801 308. Non-limiting examples that may be mentioned include pyrazolo[1,5-a]pyrid-3-ylamine, 2-acetylaminopyrazolo[1,5-a]pyrid-3-yl amine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, and the addition salts thereof.

Among the pyrimidine derivatives of which non-limiting mention may be made are the compounds described, for example, in Patent Publication Nos. DE 2 359 399; JP 88-169 571; JP 05-63124; EP 0 770 375; and WO 96/15765, for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and the addition salts thereof, and the tautomeric forms thereof, when a tautomeric equilibrium exists.

Among the pyrazole derivatives of which non-limiting mention may be made are the compounds described, for example, in Patent Publication Nos. DE 3 843 892; DE 4 133 957; WO 94/08969; WO 94/08970; FR-A-2 733 749; and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)-amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof. 4,5-Diamino-1-(β-methoxyethyl)pyrazole may also be used.

A heterocyclic base that may also be used is 2,3-diamino-6,7-dihydro-1H,5H-pyrazolo[1,2-a]pyrazol-1-one, or a salt thereof.

The at least one composition (C) according to the present disclosure may optionally comprise at least one coupler chosen from those conventionally used in the dyeing of keratin fibers.

Among these couplers, non-limiting mention may be made, for example, of meta-phenylenediamines, meta-aminophenols, meta-diphenols, naphthalene-based couplers, heterocyclic couplers, and the addition salts thereof.

Non-limiting mention may be made, for example, of 1,3-dihydroxybenzene, 1,3-dihydroxy-2-methylbenzene, 4-chloro-1,3-dihydroxybenzene, 2,4-diamino-1-(β-hydroxyethyl oxy)benzene, 2-amino-4-(β-hydroxyethylamino) 1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methyl-indole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazo-5-one, 1-phenyl-3-methylpyrazol-5-one, 2,6-dimethylpyrazolo[1,5-b]-1,2,4-triazole, 2,6-dimethyl[3,2-c]-1,2,4-triazole, 6-methylpyrazolo[1,5-a]benzimidazole, the acid addition salts thereof, and mixtures thereof.

For example, the addition salts of the at least one oxidation base and at least one coupler that may be used in the context of the present disclosure are chosen, for example, from the acid addition salts such as the hydrochlorides, hydrobromides, sulfates, citrates, succinates, tartrates, lactates, tosylates, benzenesulfonates, phosphates, and acetates.

The at least one oxidation base may be present in an amount ranging from 0.0001% to 10% by weight relative to the total weight of the composition, for example from 0.005% to 5% by weight relative to the total weight of the composition.

The at least one coupler, when present, may be present in an amount ranging from 0.0001% to 10% by weight relative to the total weight of the composition, for example from 0.005% to 5% by weight relative to the total weight of the composition.

As regards the direct dyes, these dyes may be chosen, for example, from ionic and nonionic species, for instance cationic or nonionic species.

Non-limiting examples of suitable direct dyes that may be mentioned include azo; methine; carbonyl; azine; nitro (hetero)aryl; tri(hetero)arylmethane; porphyrin; phthalocyanin direct dyes, and natural direct dyes, alone or as mixtures.

For instance, the azo dyes may comprise an —N=N— function, the two nitrogen atoms of which are not simultaneously engaged in a ring. However, one of the two nitrogen atoms of the sequence —N=N— may be engaged in a ring as well.

The dyes of the methine family are, for example, compounds comprising at least one sequence chosen from >C=C< and —N=C<, the two atoms of which are not simultaneously engaged in a ring. However, one of the nitrogen or carbon atoms of the sequences may be engaged in a ring as well. For example, the dyes of this family are derived from compounds of the type such as methines, azomethines, mono- and diarylmethanes, indoamines (or diphenylamines), indophenols, indoanilines, carbocyanins, azacarbocyanins, and isomers thereof, diazacarbocyanins, and isomers thereof, tetraazacarbocyanins, and hemicyanins.

As regards the dyes of the carbonyl family, non-limiting mention may be made of acridone, benzoquinone, anthraquinone, naphthoquinone, benzanthrone, anthranthrone, pyranthrone, pyrazolanthrone, pyrimidinoanthrone, flavanthrone, idanthrone, flavone, (iso)violanthrone, isoindolinone, benzimidazolone, isoquinolinone, anthrapyridone, pyrazoloquinazolone, perinone, quinacridone, quinophthalone, indigoid, thioindigo, naphthalimide, anthrapyrimidine, diketopyrrolopyrrole, and coumarin.

As regards the dyes of the cyclic azine family, non-limiting mention may be made of azine, xanthene, thioxanthene, fluorindine, acridine, oxazine, dioxazine, thiazine, dithiazine, and pyronin.

The nitro (hetero) aromatic dyes may be, for example, nitrobenzene or nitropyridine direct dyes.

As regards the dyes of porphyrin or phthalocyanin type, it is possible to use cationic or noncationic compounds, optionally comprising at least one metal or metal ion, for instance alkali metals, alkaline-earth metals, zinc, and silicon.

Non-limiting examples of suitable direct dyes that may be mentioned include, for example, nitrobenzene dyes; azo direct dyes; azomethine direct dyes; methine direct dyes; azacarbocyanin direct dyes, for instance tetraazacarbocyanins (tetraazapentamethines); quinone and, for example, anthraquinone, naphthoquinone, and benzoquinone direct dyes; azine; xanthene; triarylmethane; indoamine; indigoid; phthalocyanin direct dyes, porphyrins, and natural direct dyes, alone or as mixtures.

These dyes may be monochromophoric dyes which means comprising only one dye group, or polychromophoric, for example di- or trichromophoric; the chromophores possibly being identical or different, and from the same chemical family or otherwise. A polychromophoric dye comprises several radicals each derived from a molecule that absorbs in the visible region ranging from 400 to 800 nm. Furthermore, this absorbance of the dye generally does not involve any prior oxidation thereof, or combination with any other chemical species.

In the case of polychromophoric dyes, the chromophores may be connected together by means of at least one linker, which may be cationic or noncationic.

For example, the linker may be chosen from linear, branched and cyclic $C_1$-$C_{20}$ alkyl chains, optionally interrupted with at least one heteroatom, such as nitrogen and oxygen, and/or with at least one group comprising such an atom, such as CO and $SO_2$, optionally interrupted with at least one heterocycle that may or may not be fused to a phenyl nucleus and comprising at least one quaternized nitrogen engaged in the ring and optionally at least one other heteroatom, such as oxygen, nitrogen, and sulfur, optionally interrupted with at least one substituted or unsubstituted phenyl and naphthyl group, optionally at least one quaternary ammonium group substituted with two optionally substituted $C_1$-$C_{15}$ alkyl groups; the linker not comprising any nitro, nitroso, and peroxy groups.

If the heterocycles or aromatic nuclei are substituted, they are substituted, by way of non-limiting example, with at least one $C_1$-$C_8$ alkyl radical optionally substituted with hydroxyl, $C_1$-$C_2$ alkoxy, $C_2$-$C_4$ hydroxyalkoxy, acetylamino, and amino groups substituted with at least one $C_1$-$C_4$ alkyl radical, optionally bearing at least one hydroxyl group, and/or the two radicals possibly forming, with the nitrogen to which they are attached, a 5- or 6-membered heterocycle optionally comprising another heteroatom identical to or different, chosen from nitrogen atoms; halogens; hydroxyl groups; $C_1$-$C_2$ alkoxy radicals; $C_2$-$C_4$ hydroxyalkoxy radicals; amino radicals; amino radicals substituted with at least one identical or different $C_1$-$C_4$ alkyl radicals optionally bearing at least one hydroxyl group.

Among the benzenic direct dyes that may be used according to the present disclosure, mention may be made in a non-limiting manner of the following compounds:

1,4-diamino-2-nitrobenzene,
1-amino-2-nitro-4-β-hydroxyethylaminobenzene,
1-amino-2-nitro-4-bis(β-hydroxyethyl)aminobenzene,
1,4-bis(β-hydroxyethylamino)-2-nitrobenzene,
1-β-hydroxyethylamino-2-nitro-4-bis(β-hydroxyethylamino)benzene,
1-β-hydroxyethylamino-2-nitro-4-aminobenzene,
1-β-hydroxyethylamino-2-nitro-4-(ethyl)(β-hydroxyethyl)aminobenzene,
1-amino-3-methyl-4-β-hydroxyethylamino-6-nitrobenzene,
1-amino-2-nitro-4-β-hydroxyethylamino-5-chlorobenzene,
1,2-diamino-4-nitrobenzene,
1-amino-2-β-hydroxyethylamino-5-nitrobenzene,
1,2-bis(β-hydroxyethylamino)-4-nitrobenzene,
1-amino-2-tris(hydroxymethyl)methylamino-5-nitrobenzene,
1-hydroxy-2-amino-5-nitrobenzene,
1-hydroxy-2-amino-4-nitrobenzene,
1-hydroxy-3-nitro-4-aminobenzene,
1-hydroxy-2-amino-4,6-dinitrobenzene,
1-β-hydroxyethyloxy-2-β-hydroxyethylamino-5-nitrobenzene,
1-methoxy-2-β-hydroxyethylamino-5-nitrobenzene,
1-β-hydroxyethyloxy-3-methylamino-4-nitrobenzene,
1-β,γ-dihydroxypropyloxy-3-methylamino-4-nitrobenzene,
1-β-hydroxyethylamino-4-β,γ-dihydroxypropyloxy-2-nitrobenzene,
1-β,γ-dihydroxypropylamino-4-trifluoromethyl-2-nitrobenzene,
1-β-hydroxyethylamino-4-trifluoromethyl-2-nitrobenzene,
1-β-hydroxyethylamino-3-methyl-2-nitrobenzene,
1-β-aminoethylamino-5-methoxy-2-nitrobenzene,
1-hydroxy-2-chloro-6-ethylamino-4-nitrobenzene,
1-hydroxy-2-chloro-6-amino-4-nitrobenzene,
1-hydroxy-6-bis(β-hydroxyethyl)amino-3-nitrobenzene,
1-β-hydroxyethylamino-2-nitrobenzene, and
1-hydroxy-4-β-hydroxyethylamino-3-nitrobenzene.

Among the azo, azomethine, methine, and tetraazapentamethine direct dyes that may be used according to the present disclosure, non-limiting mention may be made of the cationic dyes described in Patent Publication Nos. WO 95/15144; WO 95/01772; EP 714 954; FR 2 189 006, FR 2 285 851; FR 2 140 205; EP 1 378 544; and EP 1 674 073.

Thus, non-limiting mention may be made of, for example, the dyes of formulae (I) to (IV), and, for example compounds of formulae (I), (II), (III), (III') and (IV):

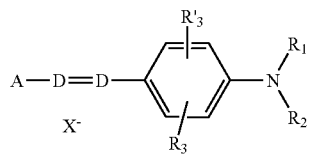
(I)

wherein:

D is chosen from a nitrogen atom and —CH groups, $R_1$ and $R_2$, which may be identical or different, are chosen from a hydrogen atom; $C_1$-$C_4$ alkyl radicals, which may be substituted with a group chosen from —CN, —OH, and —NH$_2$ radicals, or form, with a carbon atom of the benzene ring, a heterocycle optionally comprising oxygen or nitrogen, which may be substituted with at least one $C_1$-$C_4$ alkyl radical; and 4'-aminophenyl radicals, $R_3$ and $R_{13}$, which may be identical or different, are chosen from a hydrogen atom, a halogen atom chosen from chlorine, bromine, iodine, and fluorine, and cyano, $C_1$-$C_4$ alkyl, $C_1$-$C_4$ alkoxy, and acetyloxy radicals, X$^-$ is an anion chosen, for example, from chloride, methyl sulfate, and acetate, A is a group chosen from structures $A_1$ to $A_{18}$ below:

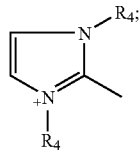
$A_1$

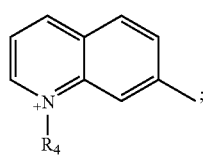
$A_2$

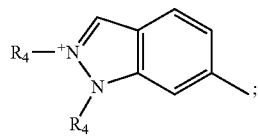
$A_3$

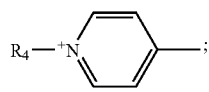
$A_4$

-continued

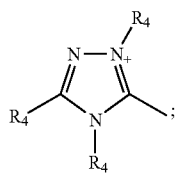
$A_5$

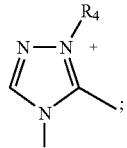
$A_6$

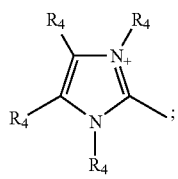
$A_7$

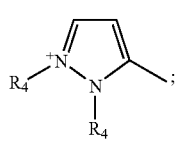
$A_8$

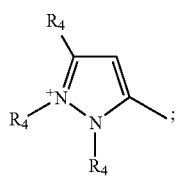
$A_9$

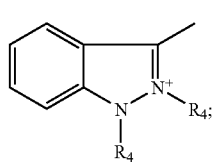
$A_{10}$

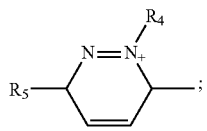
$A_{11}$

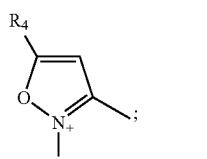
$A_{12}$

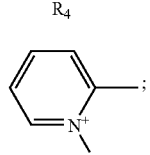
$A_{13}$

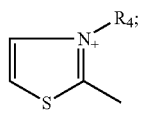
$A_{14}$

-continued

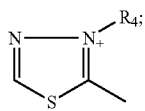
A15

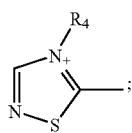
A16

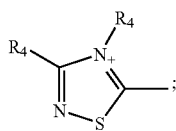
A17

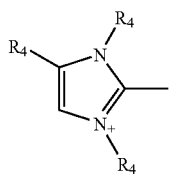
A18 wherein $R_4$ is a $C_1$-$C_4$ alkyl radical which may be substituted with a hydroxyl radical and $R_5$ is a $C_1$-$C_4$ alkoxy radical;

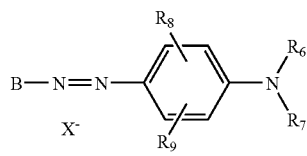
(II)

wherein:

$R_6$ is chosen from a hydrogen atom and $C_1$-$C_4$ alkyl radicals, $R_7$ is chosen from a hydrogen atom, alkyl radicals which may be substituted with a —CN radical or with an amino group, and a 4'-aminophenyl radical, or forms with $R_6$ a heterocycle optionally comprising oxygen and/or nitrogen, which may be substituted with a $C_1$-$C_4$ alkyl radical, $R_8$ and $R_9$, which may be identical or different, are chosen from a hydrogen atom, halogen atoms, such as bromine, chlorine, iodine, or fluorine, $C_1$-$C_4$ alkyl and $C_1$-$C_4$ alkoxy radicals, and a —CN radical, $X^-$ is an anion chosen, for example, from chloride, methyl sulfate, and acetate, B is a group chosen from structures $B_1$ to $B_6$ below:

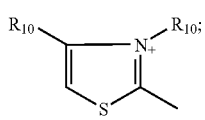
B1

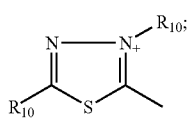
B2

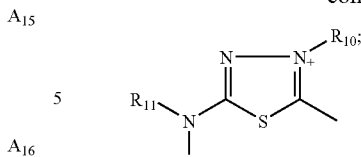
B3

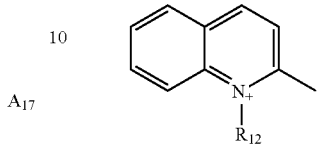
B4

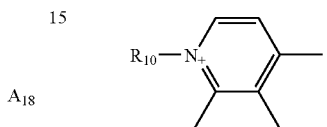
B5

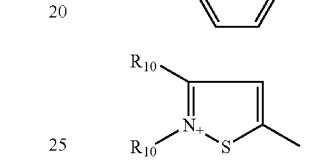
B6 wherein $R_{10}$ is chosen from $C_1$-$C_4$ alkyl radicals, $R_{11}$ and $R_{12}$, which may be identical or different, are chosen from a hydrogen atom and $C_1$-$C_4$ alkyl radicals;

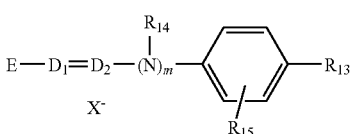
(III)

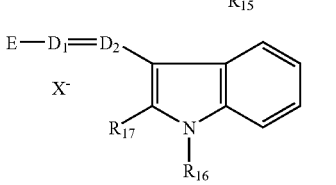
(III')

wherein:

$R_{13}$ is chosen from a hydrogen atom, $C_1$-$C_4$ alkoxy radicals, halogen atoms, such as bromine, chlorine, iodine, or fluorine, and amino radicals, $R_{14}$ is chosen from a hydrogen atom and $C_1$-$C_4$ alkyl radicals, or forms, with a carbon atom of the benzene ring, a heterocycle optionally comprising oxygen and/or substituted with at least one $C_1$-$C_4$ alkyl group, $R_{15}$ is chosen from a hydrogen atom and halogen atoms such as bromine, chlorine, iodine, or fluorine, $R_{16}$ and $R_{17}$, which may be identical or different, are chosen from a hydrogen atom and $C_1$-$C_4$ alkyl radicals, $D_1$ and $D_2$, which may be identical or different, are chosen from a hydrogen atom and —CH groups, m=0 or 1, with the condition that when $R_{13}$ is an unsubstituted amino group, then $D_1$ and $D_2$ simultaneously are —CH groups and m=0, $X^-$ is an anion chosen, for example, from chloride, methyl sulfate, and acetate, E is a group chosen from structures $E_1$ to $E_8$:

E1
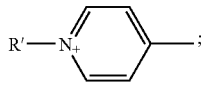

E2
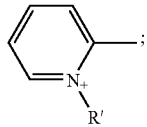

E3
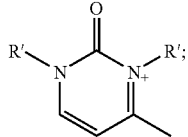

E4
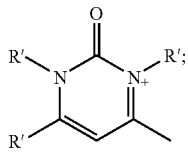

E5
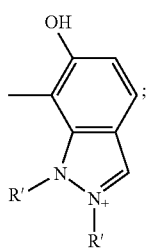

E6
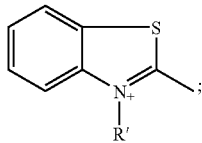

E7
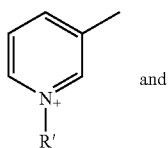 and

E8
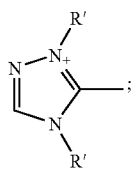

wherein R' is a $C_1$-$C_4$ alkyl radical; when m=0 and $D_1$ is nitrogen, then E may also be chosen from structure $E_9$:

wherein R' is a $C_1$-$C_4$ alkyl radical.

$$G—N=N-J \qquad (IV)$$

wherein: the symbol G is a group chosen from the structures $G_1$ to $G_3$ below:

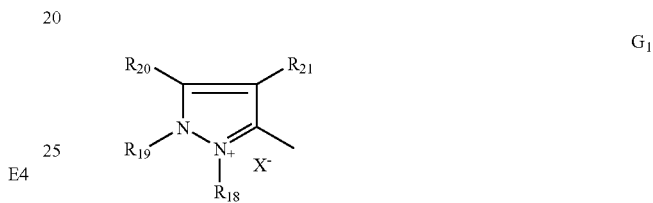

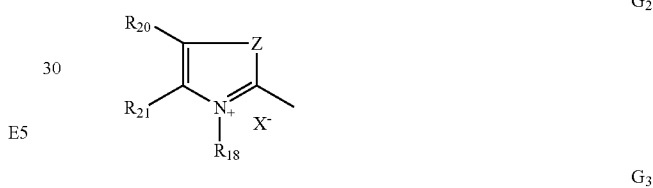

wherein:

$R_{18}$ is chosen from $C_1$-$C_4$ alkyl radicals, phenyl radicals which may be substituted with an entity chosen from $C_1$-$C_4$ alkyl radicals, and halogen atoms chosen from chlorine, bromine, iodine, and fluorine;

$R_{19}$ is chosen from $C_1$-$C_4$ alkyl radicals and phenyl radicals;

$R_{20}$ and $R_{21}$, which may be identical or different, are chosen from $C_1$-$C_4$ alkyl radicals, and phenyl radicals, or form together in $G_1$ a benzene ring substituted with at least one radical chosen from $C_1$-$C_4$ alkyl, $C_1$-$C_4$ alkoxy, and $NO_2$ radicals, or form together in $G_2$ a benzene ring optionally substituted with at least one $C_1$-$C_4$ alkyl, $C_1$-$C_4$ alkoxy, and $NO_2$ radical;

$R_{20}$ may also be a hydrogen atom;

Z is chosen from an oxygen atom, sulfur atom, and a group $—NR_{19}$;

M is chosen from —CH, —CR, R denoting $C_1$-$C_4$ alkyl, and $—NR_{22}(X^-)_r$;

K is chosen from —CH, —CR, R denoting $C_1$-$C_4$ alkyl, and $—NR_{22}(X^-)_r$;

P is chosen from —CH, —CR, R denoting $C_1$-$C_4$ alkyl, and $—NR_{22}(X^-)_r$;

r is an integer ranging from 0 to 1;

$R_{22}$ is chosen from an $O^-$ atom, $C_1$-$C_4$ alkoxy radicals, and a $C_1$-$C_4$ alkyl radical;

$R_{23}$ and $R_{24}$, which may be identical or different, are chosen from hydrogen atoms, halogens chosen from chlorine, bromine, iodine, and fluorine, and $C_1$-$C_4$ alkyl, $C_1$-$C_4$ alkoxy radical, and —$NO_2$ radical;

$X^-$ is an anion chosen, for example, from chloride, iodide, methyl sulfate, ethyl sulfate, acetate, and perchlorate;

with the proviso that, if $R_{22}$ is $O^-$, then r is zero;

if K or P or M are —N—($C_1$-$C_4$)alkyl $X^-$, then $R_{23}$ or $R_{24}$ are hydrogen atom;

if K is —$NR_{22}(X^-)_r$, then M=P=—CH or —CR;

if M is —$NR_{22}(X^-)_r$, then K=P=—CH or —CR;

if P is —$NR_{22}(X^-)_r$, then K=M and is —CH or —CR;

if Z is a sulfur atom with $R_{21}$ being a $C_1$-$C_4$ alkyl, then $R_{20}$ is not a hydrogen atom;

if Z is —$NR_{22}$ with $R_{19}$ being a $C_1$-$C_4$ alkyl, then at least one of the radicals $R_{18}$, $R_{20}$, or $R_{21}$ of the group of structure $G_2$ is not a $C_1$-$C_4$ alkyl radical;

J is:

(a) a group of structure $J_1$ below:

$J_1$ wherein:

$R_{25}$ is chosen from a hydrogen atom, a halogen atom chosen from chlorine, bromine, iodine, and fluorine, $C_1$-$C_4$ alkyl and $C_1$-$C_4$ alkoxy radicals, —OH, —$NO_2$, —$NHR_{28}$, —$NR_{29}R_{30}$, and $C_1$-$C_4$—NHCOalkyl radicals, or forms with $R_{26}$ a 5- or 6-membered ring optionally comprising at least one heteroatom chosen from nitrogen, oxygen, and sulfur;

$R_{26}$ is chosen from a hydrogen atom, a halogen atom chosen from chlorine, bromine, iodine, and fluorine, $C_1$-$C_4$ alkyl and $C_1$-$C_4$ alkoxy radicals, or forms with $R_{27}$ or $R_{28}$ a 5- or 6-membered ring optionally comprising at least one heteroatom chosen from nitrogen, oxygen, and sulfur;

$R_{27}$ is chosen from a hydrogen atom, —OH radicals, —$NHR_{28}$ radicals, and —$NR_{29}R_{30}$ radicals;

$R_{28}$ is chosen from a hydrogen atom, $C_1$-$C_4$ alkyl radicals, and $C_1$-$C_4$ monohydroxyalkyl, $C_2$-$C_4$ polyhydroxyalkyl, and phenyl radicals;

$R_{29}$ and $R_{30}$, which may be identical or different, are chosen from $C_1$-$C_4$ alkyl radicals, $C_1$-$C_4$ monohydroxyalkyl, and $C_2$-$C_4$ polyhydroxyalkyl radicals;

(b) a 5- or 6-membered nitrogenous heterocyclic group, which may comprise other heteroatoms and/or carbonyl groups and may be substituted with at least one $C_1$-$C_4$ alkyl, amino, and phenyl radical, and, for example, a group of structure $J_2$ below:

$J_2$ wherein:

$R_{31}$ and $R_{32}$, which may be identical or different, are chosen from a hydrogen atom, $C_1$-$C_4$ alkyl radicals, and a phenyl radical;

Y is chosen from a —CO— radical and a $$-\underset{\underset{CH_3}{|}}{C}=$$

radical;

n=0 or 1, with, when n is 1, U is a —CO— radical.

In structures (I) to (IV) defined above, the $C_1$-$C_4$ alkyl or alkoxy group, by way of non-limiting example, may be chosen from methyl, ethyl, butyl, methoxy, and ethoxy.

Among the above compounds, non-limiting examples include:

Among the azo direct dyes of which non-limiting mention may be made are the following dyes, described in the Colour Index International, 3rd edition:

Disperse Red 17;

Basic Red 22;

Basic Red 76;

Basic Yellow 57;

Basic Brown 16;

Basic Brown 17; and

Disperse Black 9.

Non-limiting mention may also be made of 1-(4'-aminodiphenylazo)-2-methyl-4-bis(β-hydroxyethyl)aminobenzene.

Among the quinone direct dyes of which non-limiting mention may be made are the following dyes:

Disperse Red 15;
Solvent Violet 13;
Disperse Violet 1;
Disperse Violet 4;
Disperse Blue 1;
Disperse Violet 8;
Disperse Blue 3;
Disperse Red 11;
Disperse Blue 7;
Basic Blue 22;
Disperse Violet 15;
Basic Blue 99;

and also the following compounds:
  1-N-methylmorpholiniumpropylamino-4-hydroxyanthraquinone;
  1-aminopropylamino-4-methylaminoanthraquinone;
  1-aminopropylaminoanthraquinone;
  5-β-hydroxyethyl-1,4-diaminoanthraquinone;
  2-aminoethylaminoanthraquinone; and
  1,4-bis(β,γ-dihydroxypropylamino)anthraquinone.

Among the azine dyes of which non-limiting mention may be made are the following compounds:

Basic Blue 17; and
Basic Red 2.

Among the triarylmethane dyes that may be used according to the present disclosure, non-limiting mention may be made of the following compounds:

Basic Green 1;
Basic Violet 3;
Basic Violet 14;
Basic Blue 7; and
Basic Blue 26.

Among the indoamine dyes that may be used according to the present disclosure, non-limiting mention may be made of the following compounds:

2-β-hydroxyethylamino-5-[bis(β-4'-hydroxyethyl)amino]anilino-1,4-benzoquinone;
  2-β-hydroxyethylamino-5-(2'-methoxy-4'-amino)anilino-1,4-benzoquinone;
  3-N-(2'-chloro-4'-hydroxy)phenylacetylamino-6-methoxy-1,4-benzoquinone imine;
  3-N-(3'-chloro-4'-methylamino)phenylureido-6-methyl-1,4-benzoquinone imine; and
  3-[4'-N-(ethyl,carbamylmethyl)amino]phenylureido-6-methyl-1,4-benzoquinone imine.

Among the dyes of tetraazapentamethine type that may be used according to the present disclosure, non-limiting mention may be made of the following compounds given in the table below:

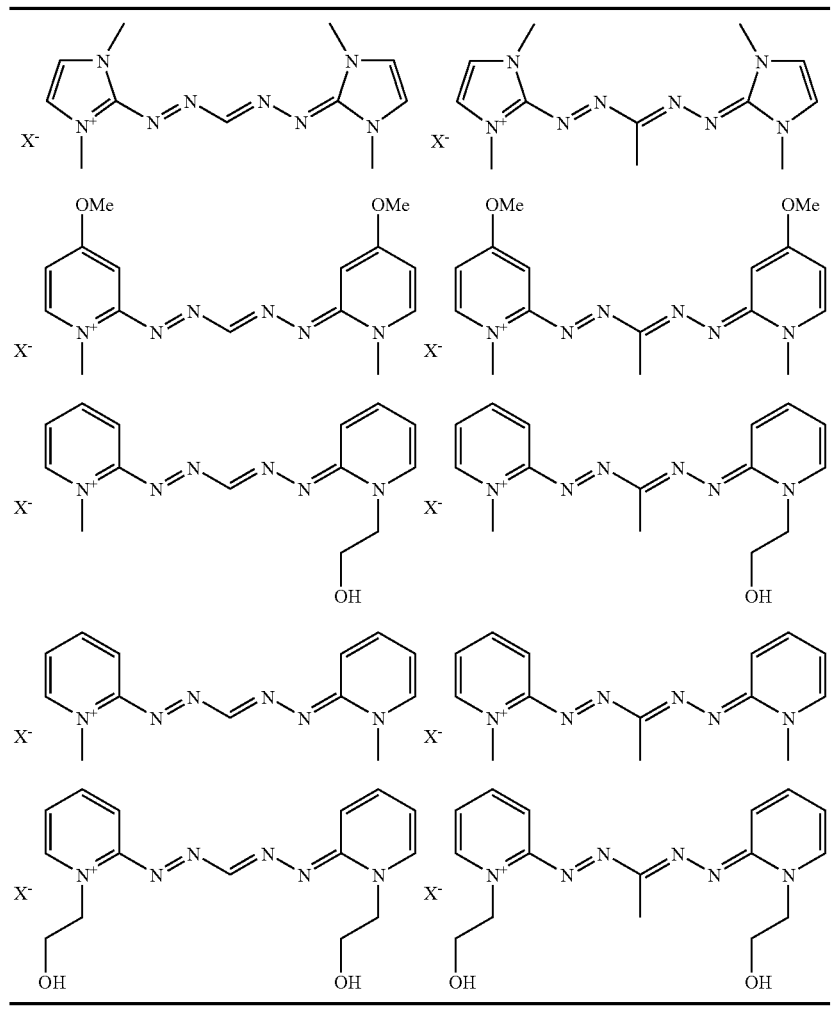

X⁻ is an anion chosen, for example, from chloride, iodide, methyl sulfate, ethyl sulfate, acetate, and perchlorate.

Among the polychromophoric dyes, non-limiting mention may be made of symmetrical or nonsymmetrical azo and/or azomethine (hydrazone) di- or trichromophoric dyes comprising for example at least one optionally fused 5- or 6-membered aromatic heterocycle, comprising at least one quaternized nitrogen atom engaged in the heterocycle and optionally at least one other heteroatom, such as nitrogen, sulfur, and oxygen, and, in another example, at least one optionally substituted phenyl or naphthyl group, optionally bearing at least one group OR with R being chosen from a hydrogen atom, an optionally substituted $C_1$-$C_6$ alkyl radical, an optionally substituted phenyl nucleus, and at least one group $N(R')_2$ with R', which may be identical or different, chosen from a hydrogen atom, an optionally substituted $C_1$-$C_6$ alkyl radical and an optionally substituted phenyl nucleus; the radicals R' possibly forming, with the nitrogen atom to which they are attached, a saturated 5- or 6-membered heterocycle, or alternatively one and/or both the radicals R' may each form, with the carbon atom of the aromatic ring located ortho to the nitrogen atom, a saturated 5- or 6-membered heterocycle.

Aromatic cationic heterocycles of which non-limiting mention may be made include 5- or 6-membered rings comprising 1 to 3 nitrogen atoms, for example, 1 to 2 nitrogen atoms, one being quaternized; the heterocycle moreover being optionally fused to a benzene nucleus. The heterocycle may optionally comprise another heteroatom other than nitrogen, for instance sulfur or oxygen.

If the heterocycles or phenyl or naphthyl groups are substituted, they are substituted, for example, with at least one $C_1$-$C_8$ alkyl radical optionally substituted with a hydroxyl, $C_1$-$C_2$ alkoxy, $C_2$-$C_4$ hydroxyalkoxy, acetylamino or amino group substituted with one or two $C_1$-$C_4$ alkyl radicals optionally bearing at least one hydroxyl group, or the two radicals possibly forming, with the nitrogen atom to which they are attached, a 5- or 6-membered heterocycle, optionally comprising another heteroatom identical to or different than nitrogen; a halogen atom; a hydroxyl group; a $C_1$-$C_2$ alkoxy radical; a $C_2$-$C_4$ hydroxyalkoxy radical; an amino radical; an amino radical substituted with one or two identical or different $C_1$-$C_4$ alkyl radicals, optionally bearing at least one hydroxyl group.

These polychromophores are connected together via at least one linker optionally comprising at least one quaternized nitrogen atom optionally engaged in a saturated or unsaturated, optionally aromatic heterocycle.

For example, the linker may be a linear, branched or cyclic $C_1$-$C_{20}$ alkyl chain, optionally interrupted with at least one heteroatom (such as nitrogen or oxygen) and/or with at least one group comprising such a heteroatom (CO or $SO_2$), optionally interrupted with at least one heterocycle optionally fused to a phenyl nucleus and comprising at least one quaternized nitrogen atom engaged in the ring and optionally at least one other heteroatom (such as oxygen, nitrogen, or sulfur), optionally interrupted with at least one substituted or unsubstituted phenyl or naphthyl group, optionally at least one quaternary ammonium group substituted with two optionally substituted $C_1$-$C_{15}$ alkyl groups; the linker not comprising any nitro, nitroso, or peroxy groups.

The bonding between the linker and each chromophore may, for example, take place via a heteroatom substituent on the phenyl or naphthyl nucleus or via the quaternized nitrogen atom of the cationic heterocycle.

The at least one dye may comprise identical or different chromophores.

As examples of such dyes, non-limiting reference may be made to Patent Publication Nos. EP 1 637 566, EP 1 619 221, EP 1 634 926, EP 1 619 220, EP 1 672 033, EP 1 671 954, EP 1 671 955, EP 1 679 312, EP 1 671 951, EP 167 952, EP 167 971, WO 06/063 866, WO 06/063 867, WO 06/063 868, WO 06/063 869, EP 1 408 919, EP 1 377 264, EP 1 377 262, EP 1 377 261, EP 1 377 263, EP 1 399 425, EP 1 399 117, EP 1 416 909, EP 1 399 116, and EP 1 671 560.

It is also possible to use the cationic direct dyes mentioned in, for example, European Patent Application No.: EP 1 006 153, which describes dyes comprising two chromophores of anthraquinone type connected via a linker of cationic type; European Patent Application Nos. EP 1 433 472, EP 1 433 474, EP 1 433 471, and EP 1 433 473, which describe identical or different dichromophoric dyes, connected via a cationic or noncationic linker, and also European Patent Application No. EP 6 291 333, which describes dyes comprising three chromophores, one of them being an anthraquinone chromophore, to which are attached two chromophores of azo or diazacarbocyanin type or an isomer thereof.

Among the natural direct dyes that may be used according to the present disclosure, non-limiting mention may be made of lawsone, juglone, alizarin, purpurin, carminic acid, kermesic acid, purpurogallin, protocatechaldehyde, indigo, isatin, curcumin, spinulosin, apigenidin, and orceins. It is also possible to use extracts or decoctions comprising these natural dyes, for example, henna-based poultices or extracts.

When they are present, the at least one direct dye is present in an amount ranging, for example, from 0.0001% to 10% by weight, further for example from 0.005% to 5% by weight, relative to the total weight of the composition.

The at least one composition (C) comprises at least one dye chosen from oxidation dyes and direct dyes. It may optionally comprise two dye compositions, one comprising the at least one oxidation dye, the other the at least one direct dye.

The at least one composition (C) may be an anhydrous or aqueous composition. For example, the at least one composition (C) comprises at least water and optionally another solvent. Those that were mentioned in the context of the description of the at least one composition (B) may, by way of non-limiting example, be used for the at least one composition (C), at the concentrations also specified for the at least one composition (B).

The at least one composition (C) may also comprise at least one organic amine having a pKb less than 12 at 25° C. Those which have been described previously may also be used in composition (C).

If the at least one composition (C) comprises at least one organic amine, then the total amount of organic amine present in the at least one anhydrous composition (A) and the at least one composition (C) is present in an amount ranging, for example, from 0.1% to 40% by weight, further for example from 0.5% to 20% by weight, relative to the weight of the compositions.

The at least one composition (C) may also comprise standard additives such as those that have been listed previously, and reference may be made thereto.

The pH of the at least one composition (C) ranges from 2 to 12, for example from 3 to 11. The pH may be adapted using acidifying or basifying agents, such as those mentioned previously.

According to at least one aspect of the present disclosure, compositions (A), (B), and (C) are applied to wet or dry keratin fibers, successively and without intermediate rinsing, for example, compositions (A) and (B), or (B) and (A) are applied, followed by the at least one composition (C).

In accordance with another aspect of the process, a composition obtained by extemporaneous mixing, before application, of compositions (A), (B), and (C) is applied to the wet or dry keratin fibers.

In these embodiments, the value of the weight ratio $R_1$ of the amounts of compositions ((A)+(C))/(B) and the value of the weight ratio $R_2$ of the amounts of compositions (A)/(C) range from 0.1 to 10, for example from 0.3 to 3.

According to one aspect of the present disclosure, the at least one composition (B) is present in an amount ranging from 50% to 70% of the total weight of the mixture of compositions (A), (B), and (C) to be applied to the hair.

The mixture present on the fibers (resulting either from the extemporaneous mixing of compositions (A), (B), and (C) or from the successive application of these compositions) is left on the fibers for a period of time sufficient for dyeing the fibers. For example, the period of time may range from 1 minute to 1 hours for example from 5 minutes to 30 minutes.

The temperature during the process may range from room temperature (from 15 to 25° C.) to 80° C., for example from room temperature to 60° C.

After the treatment, the human keratin fibers are optionally rinsed with water, optionally washed with a shampoo and then rinsed with water, before being dried or left to dry.

If the composition applied to the hair (comprising compositions (A), (B), and (C)) comprises aqueous ammonia, then the aqueous ammonia may be present in an amount, for example, less than or equal to 0.03% by weight relative to the final composition (expressed as $NH_3$), for example less than or equal to 0.01% by weight relative to the final composition. The final composition results from the mixing of compositions (A), (B), and (C); these mixtures being prepared before application to the keratin fibers (extemporaneous preparation) or directly on the keratin fibers (successive applications with or without premixing and without intermediate rinsing).

In at least one embodiment of the present disclosure, compositions (A), (B), and (C) do not comprise aqueous ammonia.

Another aspect of the present disclosure relates to a ready-to-use composition for dyeing human keratin fibers, comprising at least 35% by weight of at least one fatty substance, at least one organic amine having a pKb less than 12 at 25° C., at least one surfactant, at least one dye chosen from oxidation dyes and direct dyes, and at least one oxidizing agent.

Everything that has been detailed previously in the context of compositions (A), (B), and (C), with regard to the above ingredients, remains valid and reference may be made thereto.

Another aspect of the present disclosure relates to a multi-compartment device or kit comprising, in at least one first compartment, at least one anhydrous composition (A), in at least one second compartment, at least one composition (B) comprising at least one oxidizing agent, and in at least one third compartment, at least one composition (C) comprising at least one dye chosen from oxidation dyes and direct dyes.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

By way of non-limiting illustration, concrete examples of certain embodiments of the present disclosure are given below.

EXAMPLES

The following compositions were prepared (contents expressed in grams of active material):

| Anhydrous composition (A) | |
|---|---|
| Oxyethylenated (4 EO) sorbitan monolaurate | 21.67 |
| Fumed silica of hydrophobic nature | 11.11 |
| Pure monoethanolamine | 2.89 |
| Liquid petroleum jelly | 64.33 |
| Dye composition (C) | |
| para-Phenylenediamine | 6.55 |
| Resorcinol | 4.95 |
| 2-Methylresorcinol | 1.86 |
| 1-β-Hydroxyethyloxy-2,4-diaminobenzene dihydrochloride | 0.15 |
| Powdered sodium metabisulfite | 0.45 |
| Erythorbic acid | 0.31 |
| Pure monoethanolamine | 14.07 |
| Water | qs 100 |

At the time of use, the dye mixture was obtained by mixing together:

9 parts by weight of composition (A)

1 part by weight of composition (C)

10 parts by weight of an aqueous oxidizing composition comprising 6% of hydrogen peroxide at pH 2.3 and comprising about 80% water (B).

The resulting mixture, having a pH of 10, was then applied to a lock of natural hair containing 90% white hairs (NW) and to a permanent-waved NW lock (PWW).

The leave-on time was 30 minutes at room temperature.

After this time, the locks were rinsed, and then washed with an Elsève multivitamin shampoo.

No unpleasant odor was observed, either during the preparation of the dye mixture, or during the leave-on time on the locks.

The color of the hair was determined by using the L*a*b* system, with a MINOLTA CM2002® spectrophotometer.

According to this system, L* indicates the lightness. The lower the value of L*, the more intense is the color of the hair. The chromaticity coordinates are expressed by the parameters a* and b*, a* indicating the axis of red/green shades and b* the axis of yellow/blue shades.

The selectivity of the coloration is the variation of the color between natural colored hair and permed colored hair. Natural hair is representative of the nature of the hair at the root, and the permed hair is representative of the nature of the hair at the tip.

The selectivity is measured by:

ΔE, which is the color variation between a natural colored lock and a permed colored lock, is obtained from the following formula:

$$\Delta E = \sqrt{(L^*-L_o^*)^2+(a^*-a_o^*)^2+(b^*-b_o^*)^2}$$

wherein L* indicates lightness and a* and b* are the chromaticity coordinates of the natural colored locks whereas $L_o^*$ indicates the lightness and $a_o^*$ and $b_o^*$ are the chromaticity of the permed colored locks. A lower value of ΔE indicates lower selectivity of the coloration and more uniform color along the hair from the tip to the roots.

As shown by the results below, a strong, matt, sparingly selective coloration was obtained.

|     | L*    | a*   | b*   | Selectivity NW/PWW |
|-----|-------|------|------|--------------------|
| NW  | 18.99 | 2.4  | 3.5  | 1.21               |
| PWW | 17.83 | 2.07 | 3.34 |                    |

What is claimed is:

1. A process for dyeing human keratin fibers in the presence of at least one oxidizing agent, comprising:
   applying to the fibers
   at least one anhydrous cosmetic composition (A) comprising at least one fatty substance, at least one organic amine having a pKb less than 12 at 25° C., and at least one surfactant;
   at least one composition (B) comprising at least one oxidizing agent;
   at least one composition (C) comprising at least one dye chosen from oxidation dyes and direct dyes; and
   leaving the compositions on the fibers for a period of time sufficient to dye the fibers.

2. The process according to claim 1, wherein the at least one fatty substance is chosen from alkanes, fatty alcohols, fatty acids, fatty acid esters, fatty alcohol esters, mineral oils, plant oils, animal oils, synthetic oils, silicones, and waxes.

3. The process according to claim 1, wherein the at least one fatty substance is chosen from liquid petroleum jelly, polydecenes, and liquid esters.

4. The process according to claim 1, wherein the at least one fatty substance is present in an amount ranging from 10% to 99% by weight relative to the weight of the at least one anhydrous composition (A).

5. The process according to claim 1, wherein the at least one organic amine is at least partially miscible in the at least one fatty substance.

6. The process according claim 1, wherein the at least one organic amine comprises one or two functional groups chosen from primary, secondary, and tertiary amine functional groups, and at least one group chosen from linear and branched $C_1$-$C_8$ alkyl groups bearing at least one hydroxyl radical.

7. The process according to claim 1, wherein the at least one organic amine is chosen from:
   alkanolamines chosen from mono-, di-, and trialkanolamines, comprising from one to three identical or different $C_1$-$C_4$ hydroxyalkyl radicals and
   compounds of formula:

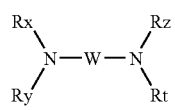

wherein W is chosen from $C_1$-$C_6$ alkylene residues optionally substituted with a hydroxyl group; Rx, Ry, Rz, and Rt, which may be identical or different, are chosen from a hydrogen atom, and $C_1$-$C_6$ alkyl, $C_1$-$C_6$ hydroxyalkyl, and $C_1$-$C_6$ aminoalkyl radicals.

8. The process according to claim 1, wherein the at least one organic amine is an alkanolamine.

9. The process according to claim 8, wherein the at least one organic amine is chosen from 2-amino-2-methyl-1-propanol and monoethanolamine.

10. The process according to claim 1, wherein the at least one organic amine is chosen from the amino acids of formula (I):

wherein R is chosen from:

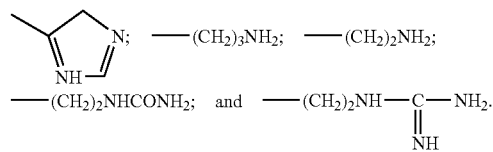

11. The process according to claim 1, wherein the at least one organic amine is chosen from arginine, histidine, and lysine.

12. The process according to claim 1, wherein the at least one organic amine is present in an amount ranging from 0.1% to 40% by weight relative to the weight of the at least one anhydrous composition (A).

13. The process according to claim 12, wherein the at least one organic amine is present in an amount ranging from 0.5% to 20% by weight relative to the weight of the at least one anhydrous composition (A).

14. The process according to claim 1, wherein the at least one surfactant is a nonionic surfactant chosen from monooxyalkylenated, polyoxyalkylenated, monoglycerolated, and polyglycerolated nonionic surfactants.

15. The process according to claim 1, wherein the at least one surfactant is present in an amount ranging from 0.1% to 50% by weight relative to the weight of the at least one anhydrous composition (A).

16. The process according to claim 15, wherein the at least one surfactant is present in an amount ranging from 0.5% to 30% by weight relative to the weight of the at least one anhydrous composition (A).

17. The process according to claim 1, wherein the at least one composition (C) further comprises at least one organic amine having a pKb less than 12 at 25° C.

18. The process according to claim 1, wherein the compositions (A), (B), and (C) are applied to the keratin fibers successively and without intermediate rinsing.

19. The process according to claim 1, wherein the compositions (B), (A), and (C) are applied to the keratin fibers successively and without intermediate rinsing.

20. The process according to claims 1, wherein a composition obtained by extemporaneous mixing, before application, of compositions (A), (B), and (C) is applied to the keratin fibers.

21. The process according to claim 1, wherein the value of the weight ratio $R_1$ of the amounts of compositions $((A)+(C))/(B)$, and the value of the weight ratio $R_2$ of the amounts of compositions $(A)/(C)$, ranges from 0.1 to 10.

22. The process according to claim 21, wherein the value of the weight ratio $R_1$ of the amounts of compositions $((A)+(C))/(B)$ and the value of the weight ratio $R_2$ of the amounts of compositions $(A)/(C)$, ranges from 0.3 to 3.

23. The process according to claim 1, wherein the at least one composition (B) is present in an amount ranging from 50% to 70% of the total weight of the mixture of compositions (A), (B), and (C).

24. The process according to claim 1, wherein the compositions (A), (B), and (C), combined on the fibers comprises at least 35% by weight of at least one fatty substance.

25. A multi-compartment device comprising,
    at least one first compartment containing at least one anhydrous composition (A) comprising at least one fatty substance, at least one organic amine having a pKb less than 12 at 25° C., and at least one surfactant;
    at least one second compartment containing at least one composition (B) comprising at least one oxidizing agent; and
    at least one third compartment containing at least one composition (C) comprising at least one dye chosen from oxidation dyes and direct dyes.

26. A ready-to-use composition for dyeing human keratin fibers, comprising at least 35% by weight of at least one fatty substance, at least one organic amine having a pKb less than 12 at 25° C., at least one surfactant, at least one dye chosen from oxidation dyes and direct dye, and at least one oxidizing agent.

\* \* \* \* \*